US009572471B2

(12) United States Patent
Basu et al.

(10) Patent No.: US 9,572,471 B2
(45) Date of Patent: Feb. 21, 2017

(54) NONWOVEN ANTIMICROBIAL SCRUB PAD

(71) Applicants: SAINT-GOBAIN ABRASIVES, INC., Worcester, MA (US); SAINT-GOBAIN ABRASIFS, Conflans-Sainte-Honorine (FR)

(72) Inventors: Soumyajit Basu, Bangalore (IN); Kottotil Mohan Das, Bangalore (IN); Rishwanth Sathyamurthy, Bangalore (IN); Anindya Agasty, Navi Mumbai (IN); Abhay Jain, Bangalore (IN)

(73) Assignees: SAINT-GOBAIN ABRASIVES, INC., Worcester, MA (US); SAINT-GOBAIN ABRASIFS, Conflans-Sainte-Homorine (FR)

( * ) Notice: Subject to any disclaimer, the term of this patent is extended or adjusted under 35 U.S.C. 154(b) by 0 days.

(21) Appl. No.: 14/824,874

(22) Filed: Aug. 12, 2015

(65) Prior Publication Data
US 2016/0045094 A1 Feb. 18, 2016

(30) Foreign Application Priority Data

Aug. 13, 2014 (IN) ............................ 3970/CHE/2014

(51) Int. Cl.
| *A01N 25/34* | (2006.01) |
| *A47L 13/17* | (2006.01) |
| *A01N 25/10* | (2006.01) |
| *A01N 55/02* | (2006.01) |
| *A01N 43/40* | (2006.01) |
| *A01N 59/16* | (2006.01) |

(52) U.S. Cl.
CPC .............. *A47L 13/17* (2013.01); *A01N 25/10* (2013.01); *A01N 25/34* (2013.01); *A01N 43/40* (2013.01); *A01N 55/02* (2013.01); *A01N 59/16* (2013.01)

(58) Field of Classification Search
CPC ...................................................... A01N 25/34
See application file for complete search history.

(56) References Cited

U.S. PATENT DOCUMENTS

| 4,401,712 A | 8/1983 | Morrison |
| 4,948,585 A | 8/1990 | Schlein |
| (Continued) | | |

FOREIGN PATENT DOCUMENTS

| KR | 100447276 B1 | 9/2004 |
| WO | 99/51401 A1 | 10/1999 |
| (Continued) | | |

OTHER PUBLICATIONS

Gerstein, Terry, M.S., 'Clear Zinc Pyrithione Preparations', J. Soc. Cosmet. Che., 23, pp. 99-114, Feb. 3, 1972.
(Continued)

*Primary Examiner* — Carlos Azpuru
(74) *Attorney, Agent, or Firm* — Abel Law Group, LLP; Joseph P Sullivan

(57) ABSTRACT

An abrasive article comprising a nonwoven substrate material impregnated with a first and second formulation. The first and second formulations have broad spectrum antimicrobial effectiveness against one or more microbial organisms. The first and second formulations include the same or different polymer compositions, which include one or more antimicrobial agents and abrasive particles uniformly dispersed in the polymer compositions.

20 Claims, 7 Drawing Sheets

(56) References Cited

U.S. PATENT DOCUMENTS

| | | |
|---|---|---|
| 5,071,648 A | 12/1991 | Rosenblatt |
| 6,042,877 A | 3/2000 | Lyon et al. |
| 6,299,520 B1 * | 10/2001 | Cheyne, III ........... A01N 25/34 451/532 |
| 6,365,169 B1 | 4/2002 | Rosenblatt |
| 8,188,029 B2 | 5/2012 | Nekmard et al. |
| 2009/0075547 A1 | 3/2009 | Rotter |
| 2009/0269379 A1 | 10/2009 | Herbst |
| 2010/0175209 A1 | 7/2010 | Gormley et al. |
| 2011/0277261 A1 | 11/2011 | Hasket et al. |
| 2012/0103839 A1 | 5/2012 | Sawalski |

FOREIGN PATENT DOCUMENTS

| | | |
|---|---|---|
| WO | 2006083570 A2 | 8/2006 |
| WO | 2009039348 A1 | 3/2009 |
| WO | 2016025607 A1 | 2/2016 |

OTHER PUBLICATIONS

Zinc Pyrithione, Pesticides: Reregistration, 2 pages, http://www.epa.gov/oppsrrd1/reregistration/zinc-pyrithione/, printed Jul. 30, 2014.
International Search Report from PCT/US2015/044871 dated Nov. 27, 2015, 1 pg.

* cited by examiner

NONWOVEN ANTIMICROBIAL SCRUB PAD

CROSS-REFERENCE TO RELATED APPLICATION

The application claims priority under 35 U.S.C. §119(a) to, and incorporates herein by reference in its entirety for all purposes, Indian application 3970/CHE/2014, filed Aug. 13, 2014, entitled "NONWOVEN ANTIMICROBIAL SCRUB PAD", to Soumyajit BASU et al., which application is incorporated by reference herein in its entirety.

FIELD OF THE INVENTION

The present invention relates generally to nonwoven abrasive articles and, more particularly, to nonwoven abrasive articles having an antimicrobial agent.

BACKGROUND

Nonwoven abrasive articles used for cleaning, such as nonwoven abrasive scrub pads, can harbor microorganisms such as bacteria and fungi that can thrive and rapidly multiply in moist environments. Consequently, it is desirable to use materials that are effective at cleaning and that control or prevent the growth of unwanted microorganisms on nonwoven abrasive articles. Although various approaches have been taken to try to solve the problem of microbial growth on nonwoven abrasive articles used for cleaning, such approaches have not produced nonwoven abrasive articles that have long lasting effects on a broad spectrum of organisms.

Therefore, there continues to be a demand for improved nonwoven abrasive articles.

BRIEF DESCRIPTION OF THE DRAWINGS

The present disclosure can be better understood, and its numerous features and advantages made apparent to those skilled in the art by referencing the accompanying drawings.

The use of the same reference symbols in different drawings indicates similar or identical items.

DETAILED DESCRIPTION

Figure 1:
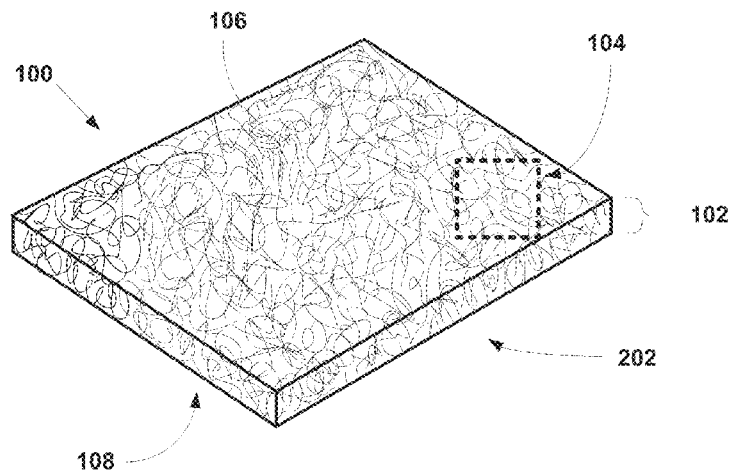
FIG. 1 includes an illustration of a perspective view of a nonwoven abrasive article according to an embodiment.

FIG. 1 includes an illustration of a perspective view of a nonwoven abrasive article 100 according to an embodiment. In particular, nonwoven abrasive article 100 can include a nonwoven substrate, and more particularly can be configured as a scrubber pad useful for cleaning in a moist environment, such as in a kitchen. In an embodiment, a nonwoven abrasive article can have a body having any regular or irregular shape. In an embodiment, a nonwoven abrasive article can have two major sides opposite each other and generally parallel to each other. In the embodiment illustrated in FIG. 1, the nonwoven abrasive article 100 can have a generally square or rectangular shape, a first surface 106, a second surface 108 generally opposite of the first surface 106, and a thickness 102 extending from the first surface 106 to the second surface 108. According to an embodiment, the nonwoven abrasive article 100 can have one or more formulations coated, dipped, sprayed, adhered to, or otherwise disposed on one or more of the first surface 106 or the second surface 108, and additionally within and throughout the thickness 102. In particular, the one or more formulations can include an antimicrobial agent.

Figure 2:
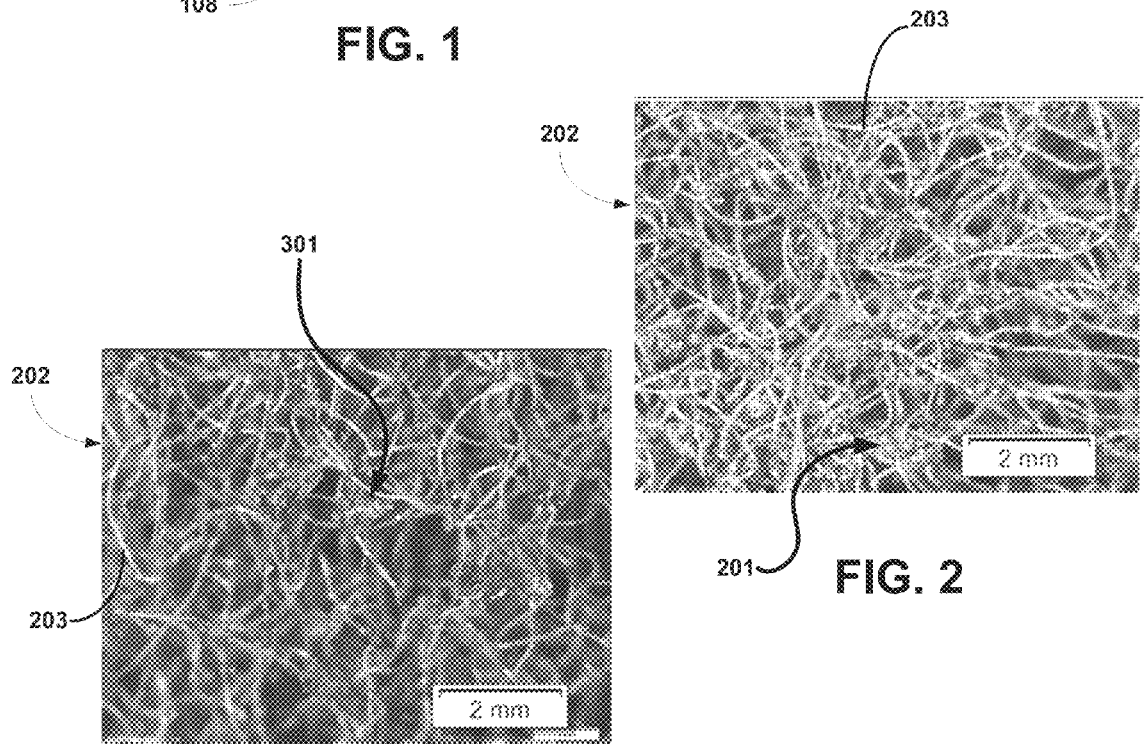
FIG. 2 includes an illustration (a magnified photograph 1.6×) of a surface view of a callout portion of the embodiment of FIG. 1.

FIG. 2 includes an illustration of a surface view of a callout portion 104 of the nonwoven abrasive article 100 of FIG. 1. The nonwoven abrasive article 100 can include a formulation having one or more antimicrobial agents disposed on the surface of the nonwoven abrasive article 100. As illustrated, a formulation 201 including an antimicrobial agent can be coated on portions of an interlocked web 202 formed of nonwoven filaments 203.

Figure 3:
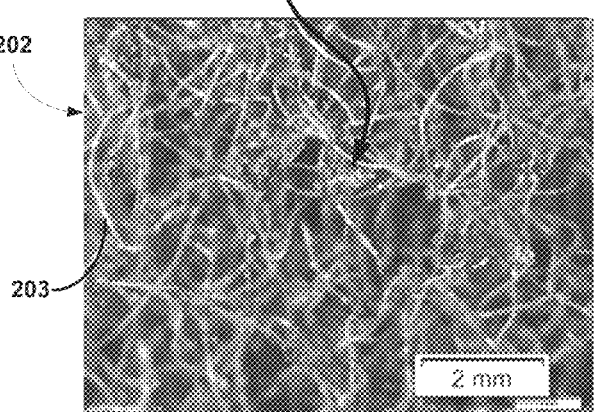
FIG. 3 includes an illustration (a magnified photograph 1.6×) of an interior view of a callout portion of the embodiment of FIG. 1.

FIG. 3 includes an illustration of an interior view of the callout portion 104 of the nonwoven abrasive article 100 of FIG. 1. The nonwoven abrasive article 100 can include a formulation having one or more antimicrobial agents disposed within and throughout the thickness 102 of the nonwoven abrasive article 100, as represented by FIG. 3. As illustrated, a formulation 301 including one or more antimicrobial agents can be coated on portions of an interlocked web 202 formed of nonwoven filaments 203. In an embodiment, the formulation 301 disposed within and throughout the thickness 102 can be the same or different from the formulation 201 disposed on the one or more surfaces 106, 108 of the nonwoven abrasive article 100.

Figure 4:
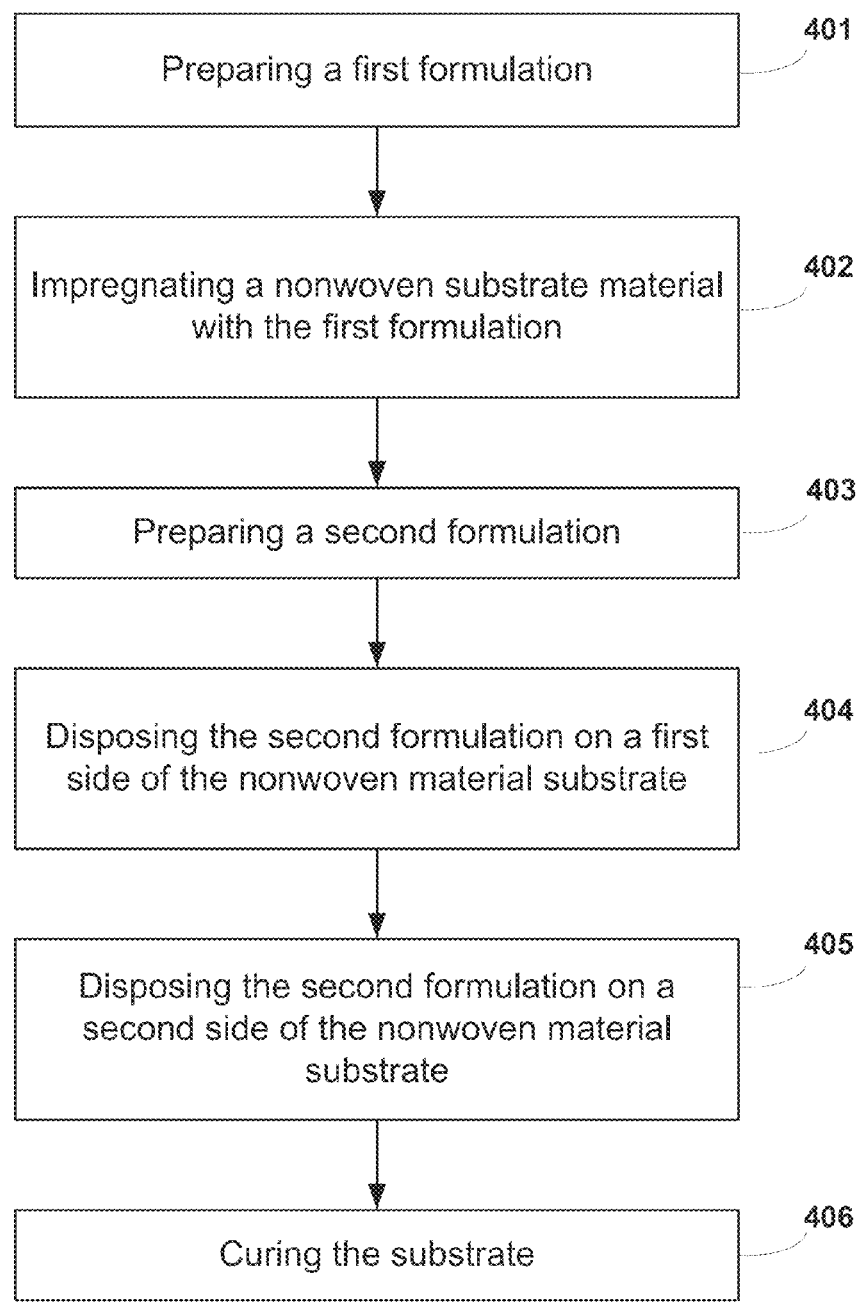
FIG. 4 includes a flow diagram including a method of making a nonwoven abrasive article according to an embodiment.

FIG. 4 includes an illustration of a flow diagram for a method of making an abrasive article having an antimicrobial agent in accordance with an embodiment. Step 401 of FIG. 4 includes preparing a first formulation. In a particular embodiment, a dip coating formulation can be prepared in step 401. In step 402, impregnating the nonwoven substrate material with the first formulation occurs. In a particular embodiment, the impregnation is accomplished by dipping the nonwoven substrate material in the first formulation and squeezing out excess formulation. Step 403, includes preparing a second formulation. In a particular embodiment, a spray formulation can be prepared in step 403. Step 404 includes disposing the second formulation on a first side of the nonwoven substrate material. In a particular embodiment, disposing the second formulation is accomplished by spraying the second formulation. Step 405 includes disposing the second formulation on a second side of the nonwoven substrate material. In a particular embodiment, disposing the second formulation is accomplished by spraying the second formulation. Step 406 includes curing the substrate to form an abrasive article. In a particular embodiment, the curing can be accomplished by heating the saturated nonwoven material substrate in an oven so as to cure the first formulation and the second formulation.

First Formulation

In an embodiment, a nonwoven substrate material is impregnated with a first formulation, wherein the first formulation has broad spectrum antimicrobial effectiveness against one or more microbial organisms; and wherein the first formulation comprises a first antimicrobial agent and abrasive particles uniformly dispersed in a first polymer composition. In a particular embodiment, the first formulation has broad spectrum antimicrobial effectiveness against *Staphylococcus aureus* (also referred to herein as "*S. aureus*"), and one or more of *Klebsiella pneumonia* (also referred to herein as "*K. pneumonia*"), *Bacillus*, and *Escherichia coli* (also referred to herein as "*E. coli*").

Figure 6A:
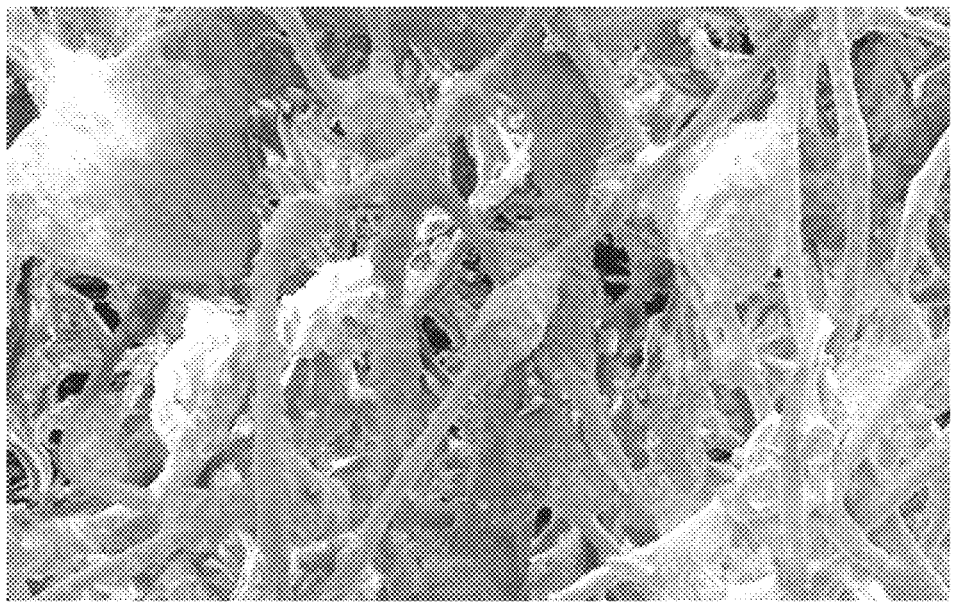
FIG. 6A includes a SEM image of a surface portion of an abrasive article according to an embodiment.

In accordance with an embodiment, the first formulation comprises a first antimicrobial agent. In a particular embodiment, a first formulation can be configured as a coating that impregnates the nonwoven substrate material and adheres to the fibers of the nonwoven substrate material throughout the thickness of the non-woven material. As described further herein, the first formulation can be applied in any suitable manner that impregnates the nonwoven substrate material in a selective or uniform manner throughout the nonwoven material. FIG. 2 and FIG. 6A illustrate a first formulation disposed on (i.e., adhered to) the fibers of the interior of a nonwoven material substrate according to an embodiment.

In accordance with an embodiment, the first formulation comprises a first antimicrobial agent. The first antimicrobial agent can comprise a compound that has antimicrobial properties as understood by those of ordinary skill in the art, such as the ability to kill (e.g., bactericidal) or inhibit the growth (e.g., bacteriostatic) of microscopic organisms such as, for example, bacteria, fungi, or protozoa. Examples of first antimicrobial agents can include triclosan (also referred to herein as "TN"), triclocarban (also referred to herein as "TCC"), polyhexamethylene, binguanide (also referred to herein as "PHMB"), salicylic acid, benzalkonium chloride, chloroxylenol, silver, pyrithiones, or any combination thereof. A first antimicrobial agent can be available in in one or more formats, such as a solution, a suspension, an emulsion, a sol, a gel, a solid, a powder, a composite, or combinations thereof. A first antimicrobial agent can be in a suitable particle size, more particularly micron sized particles, nano sized particles, or a combination thereof. In a particular embodiment, the first antimicrobial agent can include a pyrithione, and more particularly, zinc pyrithione (also referred to herein as "ZPT"). In a particular embodiment, the first antimicrobial agent can comprise pure silver, elemental silver, ionic silver, or combinations thereof. In a particular embodiment, the silver can comprise a silver salt. In a specific embodiment, the silver can be a silver solution, a silver suspension, a silver emulsion, a silver sol, a silver gel, solid silver, a silver powder, a silver composite material, or combinations thereof. In a particular embodiment, the silver can be in combination with a polymer, a polymer composite, or combinations thereof. In a particular embodiment, the first antimicrobial agent can comprise ZPT. In a particular embodiment, the first antimicrobial agent can consist essentially of ZPT. As used herein, the phrase "consist essentially of," "consisting essentially of," "consists essentially of," or any such an equivalent phrase, limits the scope of the antimicrobial agent to the specified antimicrobial agent, but the scope can include other materials that do not materially affect the characteristic of being an antimicrobial agent as defined herein. In other words, an abrasive article according to an embodiment that consists essentially of ZPT does not include another antimicrobial agent.

In an embodiment, the first antimicrobial agent can have a broad spectrum effectiveness against one or more microbial organisms. Broad spectrum antimicrobial effectiveness can be defined as capable of killing at least 75% of the population of an initial inoculation of one or more microbial organisms. Alternatively, broad spectrum effectiveness against one or microbial organisms can be defined as capable of producing a zone of inhibition around a sample of the abrasive article, wherein the zone of inhibition is at least 3 cm for a population of one or more microbial organisms. In a specific embodiment, a first antimicrobial agent possesses broad spectrum antimicrobial effectiveness when it satisfies either of the definitions of broad spectrum effectiveness. In a specific embodiment, a first antimicrobial agent possesses broad spectrum antimicrobial effectiveness when it satisfies both definitions of broad spectrum effectiveness.

In a particular embodiment, the first antimicrobial agent can have a broad spectrum antimicrobial effectiveness against *S. aureus*, and one or more of *K. pneumoniae*, *Bacillus*, and *E. coli*. Broad spectrum antimicrobial effectiveness can be defined as capable of killing at least 75% of the population of an initial inoculation of *E. coli* after 24 hours, at least 75% of the population of an initial inoculation of *K. pneumoniae* after 24 hours, and killing at least 95% of the population of an initial inoculation of *S. aureus* after 24 hours in accordance with test method ASTM: E2149-10. Alternatively, broad spectrum antimicrobial effectiveness can be defined as capable of producing a zone of inhibition around a sample of the abrasive article, wherein the zone of inhibition is at least 3 cm for a population of *S. aureus*, and one or more of *K. pneumoniae*, *Bacillus*, and *E. coli* for a 2.54 cm by 2.54 cm (2.54 $cm^2$) abrasive article sample tested according to the Kirby-Bauer antibiotic testing method (also commonly known as KB testing or disk diffusion antibiotic sensitivity testing. In a specific embodiment, a first antimicrobial agent possesses broad spectrum antimicrobial effectiveness when it satisfies either of the definitions of broad spectrum effectiveness. In a specific embodiment, a first antimicrobial agent possesses broad spectrum antimicrobial effectiveness when it satisfies both definitions of broad spectrum effectiveness.

Figure 5:
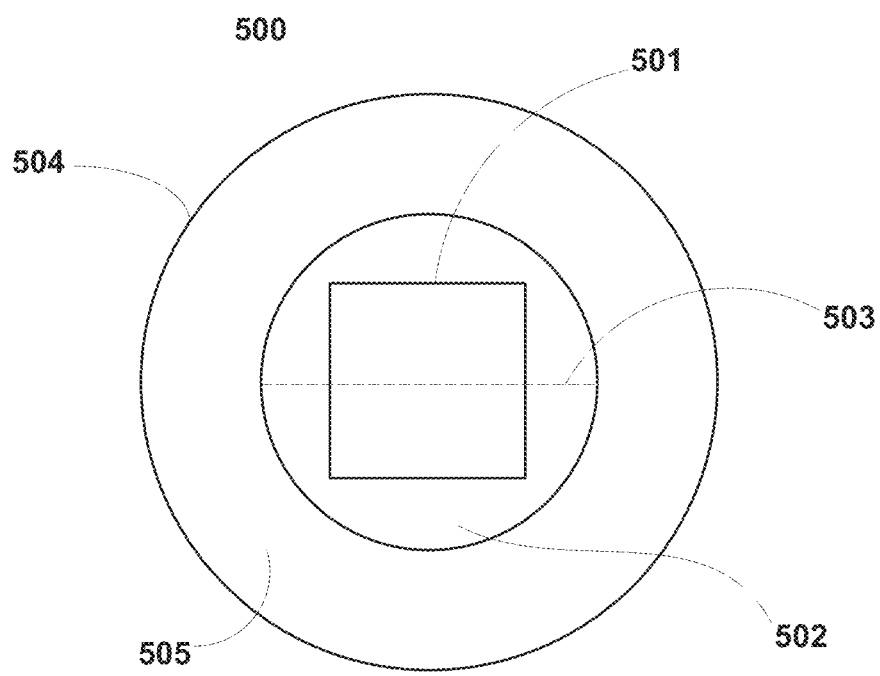
FIG. 5 includes a top view illustration of a zone of inhibition result of a nonwoven abrasive article according to an embodiment.

FIG. 5, illustrates a top view of a bacterial sample 505 contained within petri dish 504. Surrounding abrasive article 501 is a zone of inhibition 502 having a diameter 503 indicating effective antimicrobial properties of the abrasive article.

The first formulation can include a first antimicrobial agent in a particular concentration. In an embodiment, the first formulation can include a first antimicrobial agent at a concentration of at least 0.1 wt % of the total weight of the formulation, such as at a concentration of at least 0.2 wt %, at least 0.3 wt %, at least 0.4 wt %, at least 0.5 wt %, at least 0.6 wt %, at least 0.7 wt %, at least 0.8 wt %, at least 0.9 wt %, at least 1.0 wt %, at least 1.1. wt %, at least 1.2 wt %, at least 1.3 wt %, at least 1.4 wt %, or at least 1.5 wt %. In a non-limiting embodiment, the first formulation can include an antimicrobial agent at a concentration of not greater than 5.0 wt % of the total weight of the formulation, such as at a concentration of not greater than not greater than 4.5 wt %, not greater than 4.0 wt %, not greater than 3.5 wt %, not greater than 3.0 wt %, not greater than 2.5 wt %, not greater than 2.0 wt %, or not greater than 1.5 wt %. It will be appreciated that the first formulation can include an antimicrobial agent at a concentration within any range of maximum or minimum values noted above, such as within a range of from 0.1 wt % to 5.0 wt %, or within a range of from 0.5 wt % to 1.5 wt % of the total weight of the first formulation.

In an embodiment, the first formulation comprises the first antimicrobial agent and abrasive particles uniformly dispersed in a first polymer composition. In an embodiment, the first polymer composition can comprise phenolic resin, melamine formaldehyde resin, or combinations thereof. In a particular embodiment, the phenolic resin is a phenol formaldehyde resin, more particularly the phenolic resin can comprise a resole resin.

Suitable resole resins can be classified by a number of features, such as the formaldehyde to phenol ratio (F/P ratio) prior to reaction, free formaldehyde content (FFC) of the polymer after reaction, free phenol content (FPC) after reaction, gel time at a specific temperature, and the water tolerance of the resin. In an embodiment, the F/P ratio can be in a range of 0.95 to 2.5, such as 0.95 to 1.1, or 1.2 to 1.5, or 1.6 to 1.8, or 1.9 to 2.2, or a combination thereof. In an embodiment, the FFC can be in a range of 0.02% to 3.3% by weight of the resin, such as about 0.02% to 0.09%, or 0.2% to 0.45%, or 0.5% to 0.8%, or 1.0% to 1.3%, or 2.5% to 3%, or combinations thereof. In an embodiment, the FPC can be in a range of 2% to 5%, or 4% to 7%, or 12% to 15%, or 16% to 20%, or combinations thereof. In an embodiment, the gel time at 121° C. can be in range of 5 minutes to 30 minutes, such as 7-11 minutes, 8-12 minutes, 9-10 minutes, 10-12 minutes, 18-22 minutes, 19-26 minutes, or combinations thereof. In an embodiment, the water tolerance is in a range of 100% to 600%, such as 100 to 300%, 100 to 350%, 150 to 300%, 150 to 350%, 400 to 480%, 400 to 550%, 430 to 500%, or combinations thereof. In a specific embodiment, a suitable resole resin, also referred to herein as "Type 2" phenolic resin, can comprise an F/P ratio in a range of 1.9 to 2.2, a gel time at 121 ° C. in a range of 7-11 minutes; and a water tolerance in a range of 150 to 300%. In another specific embodiment, a suitable resole resin, also referred to herein as "Type 1" phenolic resin, can comprise an F/P ratio in a range of 1.6 to 1.8, a gel time at 121 ° C. in a range of 8-12 minutes; and a water tolerance in a range of 150 to 300%.

In an embodiment, the first formulation can include a first polymer composition in a particular concentration. In an embodiment, the first formulation can include a first polymer composition at a concentration of at least 10 wt % of the total weight of the first formulation, such as at a concentration of at least 22 wt %, at least 24 wt %, at least 26 wt %, at least 28 wt %, or at least 30 wt %. In a non-limiting embodiment, the first formulation can include a first polymer composition at a concentration of not greater than 60 wt %, such as not greater than 45 wt %, not greater than 40 wt %, not greater than 35 wt %, or not greater than 30 wt %. It will be appreciated that the first formulation can include a first polymer composition at a concentration within any range of maximum or minimum values noted above, such as within a range of 20 wt % to 50 wt %, or 30 wt % to 50 wt %, or 30 wt % to 40 wt % of the total weight of the first formulation.

In an embodiment, the first formulation can include a resole resin in a particular concentration. In an embodiment, the first formulation can include a resole resin at a concentration of at least 10 wt % of the total weight of the formulation, such as at a concentration of at least 22 wt %, at least 24 wt %, or at least 26 wt %. In a non-limiting embodiment, the first formulation can include a resole resin at a concentration of not greater than 60 wt %, not greater than 50 wt %, not greater than 40 wt %, not greater than 35 wt %, such as not greater than 33%, or not greater than 30 wt %. It will be appreciated that the first formulation can include a resole resin at a concentration within any range of maximum or minimum values noted above, such as within a range of 20 wt % to 40 wt %, 20 wt % to 30 wt %, or 25 wt % to 35 wt % of the total weight of the first formulation.

In an embodiment, the first formulation can include a melamine formaldehyde resin (melamine resin), such as that commercially available under the trade name POLYFIX® from Benson Polymers Ltd, (Delhi, India).

In an embodiment, the first formulation can include a melamine formaldehyde resin in a particular concentration. In an embodiment, the first formulation can include a melamine resin at a concentration of at least 2.0 wt % of the total weight of the formulation, such as at a concentration of at least 5.0 wt %, at least 7 wt %, at least 8.0 wt %, at least 10 wt %, at least 15 wt %. In a non-limiting embodiment, the first formulation can include a melamine resin at a concentration of not greater than 20.0 wt %, not greater than 15.0 wt %, not greater than 10 wt %, not greater than 9 wt %, or not greater than 8.0 wt %. It will be appreciated that the first formulation can include a melamine resin at a concentration within any range of maximum or minimum values noted above, such as within a range of 7.0 wt % to 10.0 wt %, or within a range of 8.0 wt % to 9.0 wt % of the total weight of the first formulation.

A plurality of abrasive particles can be included in the first formulation. The term abrasive particles, as used herein also encompasses abrasive grains, abrasive agglomerates, abrasive aggregates, green-unfired abrasive aggregates, shaped abrasive particles, and combinations thereof. As described herein, the plurality of abrasive particles can be dispersed in a slurry coat of the first formulation. Thus, the abrasive particles can be disposed on the first formulation, be at least partially embedded in the first formulation, or a combination thereof. The abrasive particles can generally have a Mohs hardness of greater than about 3, and preferably in a range from about 3 to about 10. For particular applications, the abrasive particles can have a Mohs hardness of at least 5, 6, 7, 8, or 9. In a specific embodiment, the abrasive particles have a Mohs hardness of 9. In another specific embodiment, the abrasive particles have a Mohs hardness of 6.5 to 7.5. Suitable abrasive particles include non-metallic, inorganic solids such as carbides, oxides, nitrides, silicates & aluminosilicates and certain carbonaceous materials. Oxides can include silicon oxide (such as quartz, cristobalite and glassy forms), cerium oxide, zirconium oxide, and various forms of aluminum oxide (including fused aluminas, sintered aluminas, seeded and non-seeded sol-gel aluminas). Carbides and nitrides can include silicon carbide, aluminum carbide, aluminum nitride, aluminium oxynitride, boron nitride (including cubic boron nitride), titanium carbide, titanium nitride, and silicon nitride. Carbonaceous materials can include diamond, which broadly includes synthetic diamond, diamond-like carbon, and related carbonaceous materials such as fullerite and aggregate diamond nanorods. Suitable abrasive particles can also include a wide range of naturally occurring mined minerals, such as garnet, cristobalite, quartz, corundum, feldspar, or the like, and combinations thereof. In particular embodiments, the abrasive particles can be diamond, silicon carbide, aluminum oxide, cerium oxide, or combinations thereof. Abrasive particles can be mixtures of two or more different abrasive particles or can be a single type of abrasive particle.

In an embodiment, the first formulation can include silica, emery, garnet, aluminum oxide, silicon carbide, or combinations thereof. The abrasive particles can be of any desired size or shape. In a specific example, the first formulation can include garnet particles having a mesh size of at least #120, or at least #220, at least #240. In an embodiment, garnet particles can include a mesh size of not greater than #400. It will be appreciated that garnet particles can have a mesh size within any minimum or maximum range indicated above, and in a particular embodiment, can include a combination of mesh sizes indicated above. In a more particular embodiment, the first formulation abrasive particles can consists essentially of #220 garnet.

In an embodiment, the first formulation can include abrasive particles in a particular concentration. In an embodiment, the first formulation can include abrasive particles at a concentration of at least 20.0 wt % of the total weight of the first formulation, such as at a concentration of at least at least 30 wt %, at least 35 wt %, at least 40 wt %, at least 50 wt %. In a non-limiting embodiment, the first formulation can include abrasive particles at a concentration of not greater than 70 wt %, not greater than 60 wt %, not greater than 50.0 wt %, not greater than 45.0 wt %, or not greater than 40 wt %. It will be appreciated that the first formulation can include abrasive particles at a concentration within any range of maximum or minimum values noted above. In a particular embodiment, the second formulation can include abrasive particles at a concentration within a range of 40.0 wt % to 30.0 wt % of the total weight of the first formulation.

The first formulation can include one or more fillers. The filler can be a single type of filler or a mixture of fillers. The filler can serve to increase the Young's modulus of the first formulation. The filler can serve to modify the pH of the first formulation. Suitable fillers can be synthetic materials or naturally occurring materials. A filler can be an inorganic or organic material. In a particular embodiment, the first formulation can include a filler, such as calcium carbonate.

In an embodiment, the first formulation can include a filler in a particular concentration. In an embodiment, the first formulation can include a filler at a concentration of at least 5.0 wt % of the total weight of the first formulation, such as at a concentration of at least 10.0 wt %, at least 15 wt %. In a non-limiting embodiment, the first formulation can include a filler at a concentration of not greater than 30 wt %, not greater than 25 wt %, not greater than 20 wt %, or not greater than 15.0 wt % of the total weight of the first formulation. It will be appreciated that the first formulation can include a filler at a concentration within any range of maximum or minimum values noted above, such as within a range of 10 wt % to 15 wt % of the total weight of the first formulation.

In an embodiment, the first formulation can include water in a particular concentration. In an embodiment, the first formulation can include water at a concentration of at least 2.0 wt % of the total weight of the first formulation, such as at a concentration of at least 4.0 wt %, at least 8.0 wt %, at least 10.0 wt %, at least 12.0 wt %, or at least 13 wt %. In a non-limiting embodiment, the first formulation can include water at a concentration of not greater than 25 wt %, not greater than 20.0 wt %, not greater than 18.0 wt %, not greater than 16.0 wt %, or not greater than 15.0 wt %. It will be appreciated that the first formulation can include water at a concentration within any range of maximum or minimum values noted above, such as within a range of 10.0 wt % to 20.0 wt %.

As will be appreciated, water can be added to the first formulation to adjust viscosity or for varying concentrations of materials of the first formulation such as, in an embodiment, changes in the concentration of the antimicrobial agent.

The first formulation can also comprise other additives that aid the manufacture of the abrasive article. Other additives can include clays; such as kaolin; salts, pH modifiers, adhesion promoters, thickeners, plasticizers, lubricants, wetting agents, antistatic agents, pigments, dyes, coupling agents; flame retardants, degassing agents, antidusting agents, thixotropic agents, rheology modifiers, initiators, surfactants, chain transfer agents, stabilizers, dispersants, reaction mediators, dyes, colorants, and defoamers.

In an embodiment, a first formulation can comprise one or more rheology modifiers. A rheology modifier can be used to influence the viscosity of the polymer binder composition and thus influence the distribution of the abrasive particles on the surface of, or throughout the body of, the nonwoven material substrate. In an embodiment, a rheology modifier can be a single type of rheology modifier or a mixture of rheology modifiers. In an embodiment, the first formulation can include a wetting agent.

In an embodiment, the wetting agent can be in a particular concentration. In an embodiment, the first formulation can include a wetting agent in a concentration of at least 0.05 wt % of the total weight of the formulation. In a non-limiting embodiment, the first formulation can include a wetting agent in a concentration of not greater than 2.0 wt %, such as not greater than 1.5 wt %, of the total weight of the first formulation. In will be appreciated that the first formulation can include a wetting agent at a concentration within any range of maximum or minimum values noted above, such as with a range of 0.05 wt % to 1.5 wt % of the total weight of the first formulation.

In an embodiment, the first formulation can include a defoamer in a particular concentration. In an embodiment, the first formulation can include a defoamer in a concentration of at least 0.1 wt % of the total weight of the first formulation, such as at a concentration of at least 0.2 wt %. In a non-limiting embodiment, the first formulation can include a defoamer at a concentration of not greater than 0.5 wt %, such as not greater than 0.4 wt %, or not greater than about 0.3 wt %. In will be appreciated that the first formulation can include a defoamer at a concentration within any range of maximum or minimum values noted above, such as with a range of 0.1 wt % to 0.3 wt % of the total weight of the first formulation.

In an embodiment, the first formulation can include a pigment. In a particular embodiment, the pigment can include a green pigment. In an embodiment, the first formulation can include a pigment in a particular concentration. In an embodiment, the first formulation can include a pigment in a concentration of at least 0.1 wt % of the total weight of the formulation, such as at least 0.3 wt %. In a non-limiting embodiment, the first formulation can include a wetting agent in a concentration of not greater than 2.0 wt %, not greater than 1.0 wt %, or not greater than 0.7 wt % of the total weight of the first formulation. In will be appreciated that the first formulation can include a pigment in a concentration within any range of maximum or minimum values noted above, such as with a range of 0.3 wt % to 0.7 wt % of the total weight of the first formulation.

Second Formulation

In an embodiment, a nonwoven substrate material is impregnated with a second formulation, wherein the second formulation has broad spectrum antimicrobial effectiveness against one or more microbial organisms; and wherein the second formulation comprises a second antimicrobial agent and abrasive particles uniformly dispersed in a second polymer composition. In a particular embodiment, the second formulation has broad spectrum antimicrobial effectiveness against *S. aureus*, and one or more of *K. pneumoniae*, *Bacillus*, and *E. coli*.

Figure 6B:
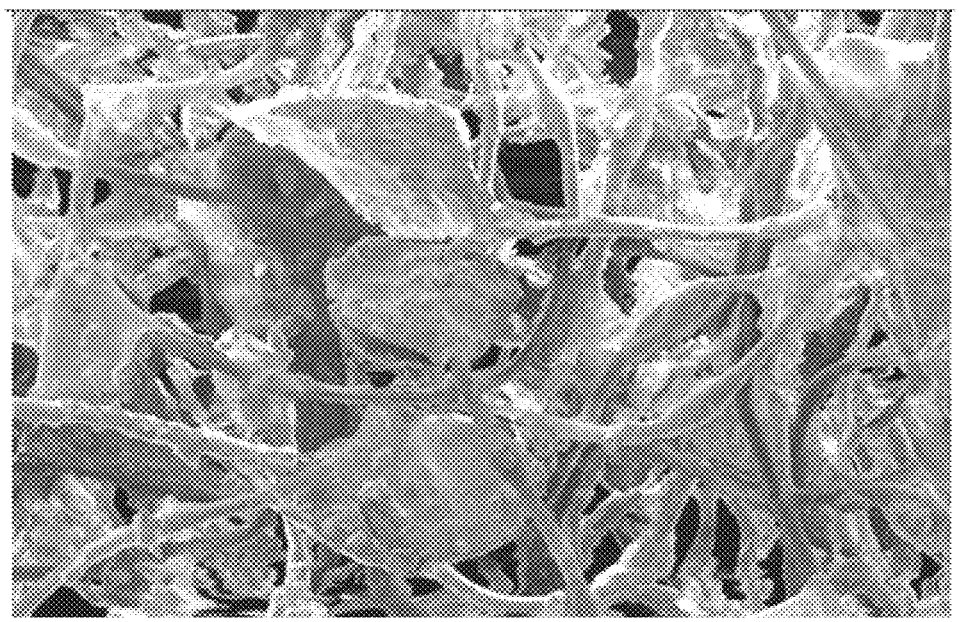
FIG. 6B includes a SEM image of an internal portion of an abrasive article according to an embodiment.

In accordance with an embodiment, the abrasive article can comprise a second formulation, alone or in combination with the first formulation. In a particular embodiment, the second formulation can be configured as a coating that is applied to and adheres the fibers of the exterior surfaces (e.g., a first side and/or a second side) of a non-woven material. In a more particular embodiment, the second formulation can be configured to be a spray coating. As will be appreciated, the second formulation can penetrate into the body of the nonwoven substrate material, and can even saturate the nonwoven substrate material if supplied in sufficient quantities. FIG. 3 and FIG. 6B illustrate a second formulation disposed on (i.e., adhered to) the fibers on an exterior surface (i.e., on a side) of a nonwoven material substrate according to an embodiment.

In accordance with an embodiment, the second formulation can include a second antimicrobial agent. The second antimicrobial agent can be the same as or different from than the first antimicrobial agent included in the first formulation. The second antimicrobial agent can comprise a compound that has antimicrobial properties as understood by those of ordinary skill in the art, such as the ability to kill (e.g., bactericidal) or inhibit the growth (e.g., bacteriostatic) of microscopic organisms such as, for example, bacteria or fungi. Examples of second antimicrobial agents can include triclosan (also referred to herein as "TN"), triclocarban (also referred to herein as "TCC"), polyhexamethylene, binguanide (also referred to herein as "PHMB"), salicylic acid, benzalkonium chloride, chloroxylenol, silver, pyrithiones, or any combination thereof. A second antimicrobial agent can be available in in one or more formats, such as a solution, a suspension, an emulsion, a sol, a gel, a solid, a powder, a composite, or combinations thereof. A second antimicrobial agent can be in a suitable particle size, more particularly micron sized particles, nano sized particles, or a combination thereof. In a particular embodiment, the second antimicrobial agent can include a pyrithione, and more particularly, zinc pyrithione (ZPT). In a particular embodiment, the second antimicrobial agent can comprise pure silver, elemental silver, ionic silver, or combinations thereof. In a particular embodiment, the silver can comprise a silver salt. In a specific embodiment, the silver can be a silver solution, a silver suspension, a silver emulsion, a silver sol, a silver gel, solid silver, a silver powder, a silver composite material, or combinations thereof. In a particular embodiment, the silver can be in combination with a polymer, a polymer composite, or combinations thereof. In a particular embodiment, the second antimicrobial agent can include a pyrithione, and more particularly, zinc pyrithione (also referred to herein as "ZPT"). In a particular embodiment, the second antimicrobial agent can comprise ZPT. In a particular embodiment, the second antimicrobial agent can consist essentially of ZPT. As used herein, the phrase "consist essentially of," "consisting essentially of," "consists essentially of," or any such an equivalent phrase, limits the scope of the antimicrobial agent to the specified antimicrobial agent, but the scope can include other materials that do not materially affect the characteristic of being an antimicrobial agent as defined herein. In other words, an abrasive article according to an embodiment that consists essentially of ZPT does not include another antimicrobial agent.

The second antimicrobial agent can have broad spectrum antimicrobial effectiveness against one or more microbial organisms as defined above with respect to the first antimicrobial agent.

The second antimicrobial agent can have broad spectrum antimicrobial effectiveness against *S. aureus*, and one or more of *K. pneumoniae, Bacillus,* and *E. coli* as defined above with respect to the first antimicrobial agent.

The second formulation can include a second antimicrobial agent in a particular concentration. In an embodiment, the second formulation can include a second antimicrobial agent at a concentration of at least 0.1 wt % of the total weight of the formulation, such as at a concentration of at least 0.2 wt %, at least 0.3 wt %, at least 0.4 wt %, at least 0.5 wt %, at least 0.6 wt %, at least 0.7 wt %, at least 0.8 wt %, at least 0.9 wt %, at least 1.0 wt %, at least 1.1. wt %, at least 1.2 wt %, at least 1.3 wt %, at least 1.4 wt %, or at least 1.5 wt %. In a non-limiting embodiment, the second formulation can include an antimicrobial agent at a concentration of not greater than 5.0 wt % of the total weight of the formulation, such as at a concentration of not greater than not greater than 4.5 wt %, not greater than 4.0 wt %, not greater than 3.5 wt %, not greater than 3.0 wt %, not greater than 2.5 wt %, not greater than 2.0 wt %, or not greater than 1.5 wt %. It will be appreciated that the second formulation can include an antimicrobial agent at a concentration within any range of maximum or minimum values noted above, such as within a range of from 0.1 wt % to 5.0 wt %, or within a range of from 0.5 wt % to 1.5 wt % of the total weight of the second formulation.

In an embodiment, the second formulation comprises the second antimicrobial agent and abrasive particles uniformly dispersed in a second polymer composition. In an embodiment, the second polymer composition can comprise phenolic resin. The phenolic resin can be the same as or different from the phenolic resin of the first formulation. In a particular embodiment, the phenolic resin is a phenol formaldehyde resin, more particularly the phenolic resin can comprise a resole resin. The resole resin can be the same as or different from the resole resin of the first formulation. In a particular embodiment, the resole resin is the same as in the first formulation.

In an embodiment, the second formulation can include a resole resin in a particular concentration. In an embodiment, the second formulation can include a resole resin at a concentration of at least 10 wt % of the total weight of the formulation, such as at a concentration of at least 20 wt %, at least 24 wt %, or at least 26 wt %. In a non-limiting embodiment, the second formulation can include a resole resin at a concentration of not greater than 60 wt %, not greater than 50 wt %, not greater than 40 wt %, not greater than 35 wt % or not greater than 30 wt %. It will be appreciated that the second formulation can include a resole resin at a concentration within any range of maximum or minimum values noted above, such as within a range of 20 wt % to 40 wt %, 20 wt % to 30 wt %, or 25 wt % to 35 wt % of the total weight of the second formulation.

A plurality of abrasive particles, such as described above with respect to the first formulation, can be included in the second formulation. The abrasive particles can be the same as or different from the abrasive particles included in the first formulation. In an embodiment, the second formulation can include silica, emery, garnet, aluminum oxide, silicon carbide, or combinations thereof. The abrasive particles can be of any desired size or shape. In an embodiment, the second formulation can include garnet particles having a mesh of at least #120, or at least #220, at least #240. In an embodiment, garnet particles can include a mesh of not greater than #400. It will be appreciated that garnet particles can have a mesh size within any minimum or maximum range indicated above. In a particular embodiment, the second formulation abrasive particles can consists essentially of #240 aluminum oxide.

In an embodiment, the second formulation can include abrasive particles in a particular concentration. In an embodiment, the second formulation can include abrasive particles at a concentration of at least 20.0 wt % of the total weight of the second formulation, such as at a concentration of at least at least 30 wt %, at least 35 wt %, at least 40 wt %, at least 50 wt %,. In a non-limiting embodiment, the second formulation can include abrasive particles at a concentration of not greater than 70 wt %, not greater than 60 wt %, not greater than 50.0 wt %, not greater than 45.0 wt %, or not greater than 40 wt %. It will be appreciated that the second formulation can include abrasive particles at a concentration within any range of maximum or minimum values noted above. In a particular embodiment, the second formulation can include abrasive particles at a concentration within a range of 55.0 wt % to 45.0 wt % of the total weight of the second formulation.

In an embodiment the second formulation can include any of the one or more fillers, water, or other additives, such as rheology modifiers, defoamers, or pigments as described above with respect to the first formulation.

In an embodiment, the second formulation can include a filler, such as calcium carbonate. In an embodiment, the second formulation can include a filler in a particular concentration. In an embodiment, the second formulation can include a filler at a concentration of at least 5.0 wt % of the total weight of the formulation, such as at a concentration of at least 10.0 wt %. In a non-limiting embodiment, the second formulation can include a filler at a concentration of 30 wt %, not greater than 25 wt %, not greater than 20 wt %, or not greater than 15.0 wt % of the total weight of the second formulation. It will be appreciated that the second formulation can include a filler at a concentration within any range of maximum or minimum values noted above, such as within a range of 10 wt % to 15 wt % of the total weight of the second formulation.

In an embodiment, the second formulation can include water in a particular concentration. In an embodiment, the second formulation can include water at a concentration of at least 2.0 wt % of the total weight of the formulation, such as at a concentration of at least 4.0 wt %, at least 8.0 wt %, at least 10.0 wt %, at least 12 wt %, or at least 13 wt %. In a non-limiting embodiment, the second formulation can include water at a concentration of not greater than 25 wt %, not greater than 20.0 wt %, or not greater than 15.0 wt %. It will be appreciated that the second formulation can include an antimicrobial agent at a concentration within any range of maximum or minimum values noted above, such as within a range of 10.0 wt % to 20.0 wt %.

As will be appreciated, water can be added to the second formulation to adjust for viscosity or for varying concentrations of materials of the second formulation such as, for example, changes in the concentration of the antimicrobial agent.

In an embodiment, the second formulation can include a wetting agent. In an embodiment, the second formulation can include a wetting agent in a particular concentration. In an embodiment, the second formulation can include a wetting agent in a concentration of at least 0.05 wt % of the total weight of the formulation. In a non-limiting embodiment, the second formulation can include a wetting agent in a concentration of not greater than 2.0 wt %, or not greater than 1.5 wt %, of the total weight of the second formulation. In will be appreciated that the second formulation can include a wetting agent at a concentration within any range of maximum or minimum values noted above, such as with a range of 0.05 wt % to 1.5 wt % of the total weight of the second formulation.

In an embodiment, the second formulation can include a defoamer in a particular concentration. In an embodiment, the second formulation can include a defoamer in a concentration of at least 0.1 wt % of the total weight of the formulation, such as at a concentration of at least 0.2 wt %. In a non-limiting embodiment, the second formulation can include a defoamer at a concentration of not greater than 0.5 wt %, such as not greater than 0.4 wt %, or not greater than about 0.3 wt %. In will be appreciated that the second formulation can include a defoamer at a concentration within any range of maximum or minimum values noted above, such as with a range of 0.1 wt % to 0.3 wt % of the total weight of the second formulation.

In an embodiment, the second formulation can include a pigment. In a particular embodiment, the pigment can include a green pigment. In an embodiment, the second formulation can include a pigment in a particular concentration. In an embodiment, the second formulation can include a pigment in a concentration of at least 0.1 wt % of the total weight of the formulation, such as at least 0.3 wt %. In a non-limiting embodiment, the second formulation can include a wetting agent in a concentration of not greater than 2.0 wt %, not greater than 1.0 wt %, or not greater than 0.7 wt % of the total weight of the second formulation. In will be appreciated that the second formulation can include a pigment in a concentration within any range of maximum or minimum values noted above, such as with a range of 0.3 wt % to 0.7 wt % of the total weight of the second formulation.

Nonwoven Substrate Material

Referring back to FIG. 4, step 402 includes impregnating a nonwoven substrate material with the first formulation. A suitable nonwoven substrate material, such as for a scrubber pad, can be formed to have a particular shape. In an embodiment, the nonwoven substrate material can be in the form of a roll or a sheet, and can be cut to be a regular shape, such as round, oval, square, or can be cut to be an irregular shape, or combinations thereof. In a particular embodiment, the nonwoven substrate material can have a square shape, and more particularly a rectangular shape. In a particular embodiment, the nonwoven substrate material can be formed into a substrate for a scrubber pad, such as a kitchen scrubber pad.

The nonwoven substrate material can comprise a synthetic material, a natural material, or combinations thereof. The material can be an absorbent material, a nonabsorbent material, or combinations thereof. In an embodiment, the nonwoven material can include different variety of aliphatic and aromatic polyamide i.e., nylons and different variety of aliphatic and aromatic polyesters, or a combination thereof.

The nonwoven substrate can be of any desired weight. In a particular embodiment, the weight of the nonwoven substrate material per unit area can be in a range of about 100 GSM to 500 GSM, such as 150 GSM to 200GSM, or about 160 GSM to about 180 GSM (i.e., grams per square meter, or g/m$^2$). Suitable nonwoven substrates are comprised of fibers that are bound together by various methods or mechanisms, such as typically, by being sprayed with a binder formulation. A suitable non-limiting binder composition is shown below in Table A of the Examples. The nonwoven substrate material can have any desired suitable loft. In a specific embodiment the loft is 12-14 mm and a weight per unit area within a range of 230-250 GSM. In accordance with an embodiment, the nonwoven substrate material can include one or more binders to adhere and interlock the threads (fibers) of the nonwoven web. In a particular embodiment, the binder can include natural or synthetic rubber latex, a large range of acrylic binder, melamine formaldehyde resin, or a combination thereof. The nonwoven substrate material is cured and complete prior to application of the first formulation or the second formulation.

In an embodiment, the nonwoven substrate material can have a particular thickness. Thickness can be defined as the minimum exterior dimension of the nonwoven substrate material. In an embodiment, the nonwoven substrate material can have a thickness that is at least 1 mm, such as at least 5 mm, at least 10 mm, at least 15 mm, at least 20 mm, or even at least 25 mm. In a non-limiting embodiment, the nonwoven substrate material can have a thickness that is not greater than 100 mm, such as not greater than 50 mm, or even not greater than 30 mm. It will be appreciated that the nonwoven substrate material can have a thickness that is within a range of any minimum or maximum value noted above.

In an embodiment, the nonwoven substrate material can have a particular loft. In an embodiment, the nonwoven substrate material can have a loft of at least 5 mm, such as at least 8 mm, or at least 10 mm. In a non-limiting embodiment, the nonwoven substrate material can have a loft that is not greater than 35 mm, such as not greater than 30 mm, not greater than 20 mm, not greater than 15 mm, or even not greater than 12 mm. It will be appreciated that the nonwoven substrate material can have a loft that is within a range of any maximum or minimum value noted above, such as within a range of 8 mm to 14 mm.

In an embodiment, the nonwoven substrate material can have a particular weight per unit area, defined as grams per square meter, or GSM. In an embodiment, the nonwoven substrate material can have a weight of at least 200 GSM, such as at least 220 GSM, or at least 240 GSM. In a non-limiting embodiment, the nonwoven substrate material can have a weight per unit area of not greater than 300 GSM, such as not greater than 270 GSM, or even not greater than 250 GSM. It will be appreciated that the nonwoven substrate material can have a weight per unit area within a range of any minimum or maximum value noted above, such as within a range of 240 GSM to 250 GSM.

Method of Making

Referring back to FIG. 4, step 401 includes preparing the first formulation. The ingredients of the first formulation, as described above can, can be mixed together by any suitable means (e.g., high-shear or low shear mixer) to prepare the first formulation.

Step 402 includes impregnating the nonwoven substrate material with the first formulation. The impregnation can be accomplished by any suitable means or manner that applies a sufficient amount of the first formulation so that the nonwoven substrate material becomes thoroughly soaked with the first formulation. In an embodiment, the impregnation can be accomplished by dipping, spraying, submerging, coating, or washing the nonwoven substrate material with or in the first formulation, or combinations thereof. The impregnation can occur as a single step or multiple steps, such as multiple dipping steps or multiple spraying steps of the nonwoven substrate material, or combinations thereof. In a specific embodiment, the nonwoven fabric is dipped into the first formulation. In another embodiment, the nonwoven substrate material is sprayed with the first formulation.

Optionally, (not shown) the amount of formulation the substrate material is impregnated with can be adjusted. Adjusting the saturation of the first formulation can be accomplished by any method or mechanism that does not overly degrade the nonwoven substrate material, such as pressing, squeezing, brushing, squeegeeing, blowing, dabbing, blotting, rollering, shaking, or combinations thereof, and the like. In a specific embodiment, the impregnated nonwoven substrate material can be squeezed, such as between a pair of rollers to adjust the saturation of the impregnated nonwoven substrate material. During step 402, in an embodiment, the nonwoven substrate material can be impregnated with a specific amount of uncured first formulation. In an embodiment, the nonwoven substrate can be impregnated with at least 200 GSM, at least 300 GSM, at least 400 GSM, at least 500 GSM, at least 600 GSM, or at least 700 GSM of the first formulation. In a non-limiting embodiment, the nonwoven substrate material is impregnated with not greater than 2000 GSM, not greater than 1500 GSM, not greater than 1000 GSM, not greater than 800 GSM, not greater than 700 GSM, or not greater than 600 GSM of the first formulation. It will be appreciated that the nonwoven substrate material can be impregnated with a weight of the first formulation within any range of minimum or maximum values noted above. In a particular embodiment, the nonwoven substrate material can be impregnated with a weight of the first formulation ranging from 200 GSM to 2000 GSM.

Referring back to FIG. 4, step 403 includes preparing the second formulation. The ingredients of the second formulation, as described above, can be mixed together by any suitable means to form the second formulation.

Post Step 402 operation, Step 404 includes disposing the second formulation on a first side of the nonwoven substrate material. Step 405 includes disposing the second formulation on a second side of the nonwoven substrate material. Steps 404 and 405, similar to step 402, can be accomplished by any suitable method, such as dipping, spraying, submerging, coating, or washing the nonwoven substrate material with or in the first formulation, or combinations thereof. In a specific embodiment, step 404 and step 405 are accomplished by spraying the nonwoven substrate material with the second formulation.

During step 404, in an embodiment, a particular amount of second formulation can be disposed on the first side of the nonwoven substrate material. In a non-limiting embodiment, at least 100 GSM, such as at least 125 GSM, such as at least 150 GSM, such as at least 175 GSM, at least 200 GSM, at least 500 GSM, or at least 750 GSM of the second formulation can be disposed on the first side of the nonwoven substrate material. In a non-limiting embodiment, not greater than 1000 GSM, such as not greater than 750 GSM, not greater than 500 GSM, not greater than 350 GSM, not greater than 325 GSM, not greater than 300 GSM, not greater than 275 GSM, not greater than 250 GSM, or not greater than 200 GSM of the second formulation can be disposed on the first side of the nonwoven substrate material. It will be appreciated that the amount of second formulation disposed on the first side of the nonwoven substrate material can be within any range of minimum or maximum values noted above. In a particular embodiment, the amount of second formulation disposed on the first side of the nonwoven substrate material can be range from 100 GSM to 300 GSM.

During step 405, in an embodiment, a particular amount of uncured second formulation can be disposed on the second side of the nonwoven substrate material. In a non-limiting embodiment, at least 100 GSM, such as at least 125 GSM, at least 150 GSM, at least 175 GSM, at least 200 GSM, at least 500 GSM, or at least 750 GSM of the second formulation can be disposed on the second side of the nonwoven substrate material. In a non-limiting embodiment, not greater than 1000 GSM, such as not greater than 750 GSM, not greater than 500 GSM, not greater than 350 GSM not greater than 325 GSM, not greater than 300 GSM, not greater than 275 GSM, not greater than 250 GSM, or not greater than 200 GSM of the second formulation can be disposed on the second side of the nonwoven substrate material. It will be appreciated that the amount of second formulation disposed on the second side of the nonwoven substrate material can be within any range of minimum or maximum values noted above. In a particular embodiment, the amount of second formulation disposed on the second side of the nonwoven substrate material can be range from 100 GSM to 300 GSM.

Step 406 includes curing the nonwoven substrate material. Curing can be performed by any curing process known in the art. In a particular embodiment, curing can include passing the dip-coated and/or spray-coated web though an oven at a temperature that will sufficiently cure the first formulation and/or the second formulation, but that will not destroy the efficacy of the first or second antimicrobial agent(s). In a particular embodiment, the nonwoven substrate material can be cured at an ambient temperature of 120-160° C.

Abrasive Article

In accordance with an embodiment, the abrasive article provides abrasive performance and broad spectrum antimicrobial effectiveness against *S. aureus*, and one or more of *K. pneumoniae*, *Bacillus*, and *E. coli* as defined above with respect to the first antimicrobial agent.

Surprisingly, the broad spectrum antimicrobial effectiveness lasts over an extended period of time and/or extensive usage of the abrasive article. In an embodiment, the abrasive article possesses broad spectrum effectiveness even after extensive usage, such as even after completing 5000 cycles according to the Cyclic Abrasion Test, which equates to cleaning approximately 500 utensils or approximately 15 days of cleaning with the abrasive article. The Cyclic Abrasion Test is described in greater detail below in the Examples. Further, the abrasive article possesses broad spectrum effectiveness even after being subjected to three hours of ball milling according to the Accelerated Life Test, which is described in greater detail below in the Examples.

In an embodiment, the abrasive article can have a particular weight, defined as grams per square meter, or GSM. In an embodiment, the abrasive article can have a weight of at least at least 300 GSM, at least 500 GSM, at least 750 GSM, at least 850 GSM, or at least 1050 GSM. In a non-limiting embodiment, the abrasive article can have a weight of not greater than 3000 GSM, such as not greater than 2000 GSM, not greater than 1500 GSM, or not greater than 1300 GSM. It will be appreciated that the abrasive article can have a weight within a range of any minimum or maximum value noted above, such as within a range of 300 GSM to 3000 GSM. IN a particular embodiment, the abrasive can have a weight per unit area within a range of 1050 GSM to 1150 GSM.

The completed abrasive article can have a particular measure of nonwoven substrate material compared to the total weight of the abrasive article (which includes the combined amount of cured first formulation and cured second formulation disposed on and in the nonwoven substrate material). In accordance with an embodiment, the abrasive article can have a $GSM_{ratio}$ of the weight of the nonwoven substrate material prior to being impregnated and sprayed with the first ad second formulation ($GSM_{nonwoven}$) to the weight of the final cured abrasive article ($GSM_{final}$). In an embodiment, the abrasive article can have a GSM ratio (i.e., $GSM_{nonwoven}$:$GSM_{final}$) of at least 1:2, meaning that the weight in GSM of the final cured abrasive article has at least twice a much weight as the nonwoven substrate material from which it was formed. In an embodiment, the $GSM_{ratio}$ can be at least 1:3, at least 1:4, or at least 1:5. In a non-limiting embodiment, the $GSM_{ratio}$ can be not greater than 1:15, such as not greater than 1:6, or not greater than 1:5. It will be appreciated that the $GSM_{ratio}$ can be within a range of any minimum or maximum value noted above. In a particular embodiment, the $GSM_{ratio}$ can be within a range of 1:3 to 1:6, and more particularly within a range of 1:4 to 1:5.

EXAMPLES

Example 1

Preparation of an Abrasive Article ("Scrubber Pad")

A. Non Woven Substrate Material

Several samples of nonwoven substrate material (also called herein "nonwoven substrates") were obtained for forming inventive abrasive articles (abrasive scrubber pads). The nonwoven substrates were formed of 100% nylon interlocked web formed by a needling procedure using 0-15 mm penetration at a rate of about 10-50 stokes per unit area. The fiber of the nonwoven substrates had fiber weight in a range of about 100 GSM to about 300 GSM (i.e., grams per square meter, or $g/m^2$) as measured after the needling procedure. The nonwoven substrates were then sprayed with a binder formulation shown below in Table A. The web was then cured in an oven at about 150° C. to form the cured nonwoven substrates. The cured nonwoven substrates had a loft within a range of 12-14 mm and a weight within a range of 230-250 GSM.

TABLE A

Backing Resin Formulation

| Material | % |
|---|---|
| Acrylic Latex | 45 |
| Melamine Formaldehyde Resin | 3 |
| Catalyst 700 | 0.2 |
| Wetting Agent | 0.1 |
| Defoaming Agent | 0.1 |
| Green Pigment | 0.5 |
| Water | 51.1 |

B. Impregnation with First Formulation (Zinc Pyrithione (ZPT))

Inventive abrasive article samples were prepared using the nonwoven substrate material of part A, above, by subsequently dipping the nonwoven substrate material into a vat containing the first formulation as a dip coating (referred to hereinafter as the "dip coating") to form a dip-coated web. The dip coating formulation included anti-microbial agent zinc pyrithione (ZPT). Samples were prepared using dip coatings having 0.5 wt %, 1.0 wt %, and 1.5 wt % of ZPT as the first antimicrobial agent. The dip coating formulation is shown below in Table B for samples having ZPT concentrations of 1.5 wt %. Note that water was added part by part to adjust the viscosity of the final formulation to a number: B5 Ford viscosity cup at room temperature for 20-30 seconds and to adjust for the different concentrations of ZPT.

TABLE B

ZPT Dip Coating Formulation

| Material | wt % |
| --- | --- |
| Water | 4.5 |
| Phenol Formaldehyde Resin | 26.9 |
| Melamine Formaldehyde Resin | 8.2 |
| Defoaming Agent | 0.2 |
| Wetting Agent | 0.1 |
| Green Pigment | 0.5 |
| Dura/Calcium Carbonate | 11.5 |
| #220 Garnet | 37.6 |
| ZPT | 1.5-0.5 |
| Water | 9.0-10.0 |

C. Application of Second Formulation (Zinc Pyrithione (ZPT))

The ZPT Samples were then sprayed on both the front and back surfaces with the second formulation as a spray coating (referred to hereinafter as the "spray coating"). Samples were prepared using corresponding spray coatings having 0.5 wt %, 1.0 wt %, and 1.5 wt % of ZPT as the second antimicrobial agent. Thus, the webs were dip coated and spray coated with matching amounts of antimicrobial agent (e.g., 0.5 wt % ZPT in dip coat and 0.5 wt % in spray coat). The 5 wt % ZPT spray coating formulation is shown below in Table C. Note that water was added part by part to adjust the viscosity of the final formulation to a Ford Cup No: 5 at room temperature for 20-30 seconds.

TABLE C

ZPT Spray Formulation

| Material | wt % |
| --- | --- |
| Water | 4.0 |
| Phenol Formaldehyde Resin | 25.0 |
| Defoaming Agent | 0.2 |
| Wetting Agent | 0.1 |
| Green Pigment | 0.5 |
| Dura/Calcium Carbonate | 10.0 |
| #240 Aluminum Oxide | 50.0 |
| ZPT | 1.5-0.5 |
| Water | 8.7-9.7 |

The dip-and-spray-coated web was cured in an oven at about 120-160° C. to form cured completed inventive abrasive article sample containing ZPT as the first antimicrobial agent and as the second antimicrobial agent (referred to hereafter as "ZPT samples"). The ZPT samples each had a final loft of about 11 mm (±1 mm), and a final weight of about 1050 GSM (±50 GSM).

D. Comparative Triclosan (TN) Samples

Comparative samples were prepared by following the same procedure and materials as above except that 1.5 wt % Triclosan (TN) was used as the first antimicrobial agent in first formulation dip coating and the second antimicrobial agent in the second formulation spray coating.

E. Combined Zinc Pyrithione and Triclosan (TNZ) Samples

Comparative samples were prepared by following the same procedure and materials as above except that 1.5 wt % of a mixture of zinc pyrithione (ZPT) and Triclosan (TN) in a 1:1 ratio was used as the first antimicrobial agent in the first formulation dip coating and as the second antimicrobial agent in the second formulation spray coating.

F. Zone of Inhibition Test

Figure 7:
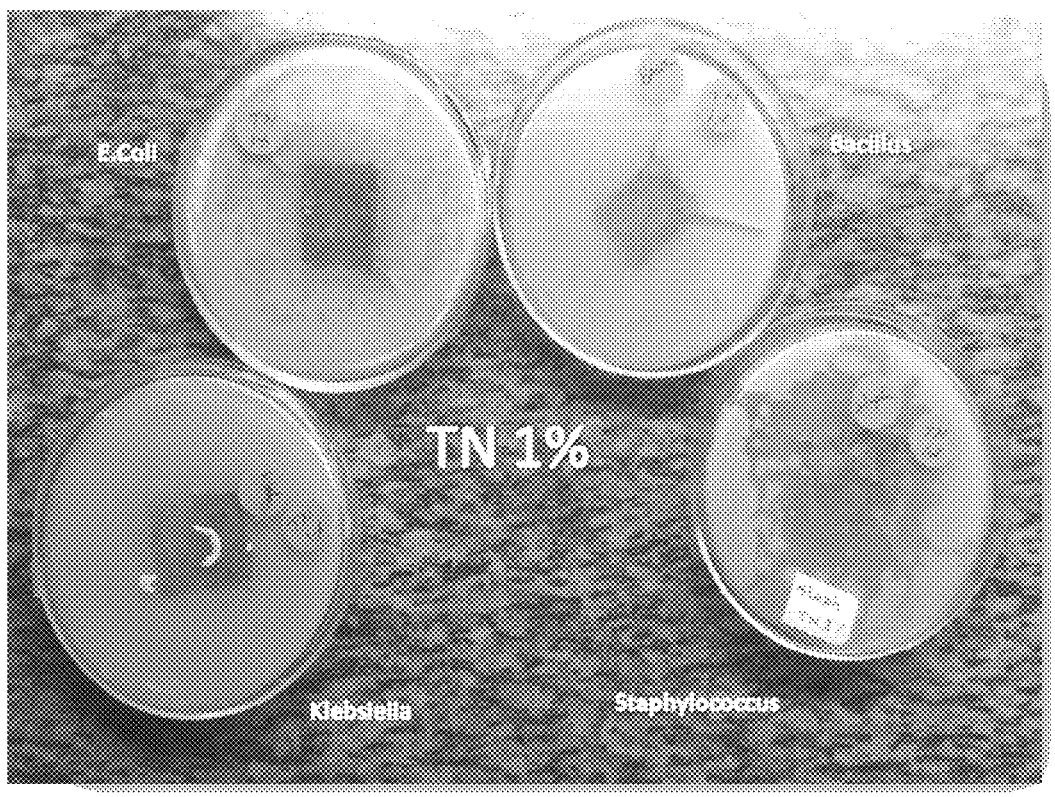
FIG. 7 includes an image of the results of zone of inhibition testing according to an embodiment including 1% triclosan ("TN") antimicrobial agent against *Klebsiella pneumonia* ("*K. pneumonia*"), *Escherichia coli* ("*E. coli*"), *Bacillus*, and *Staphylococcus aureus* ("*S. aureus*").
Figure 8:
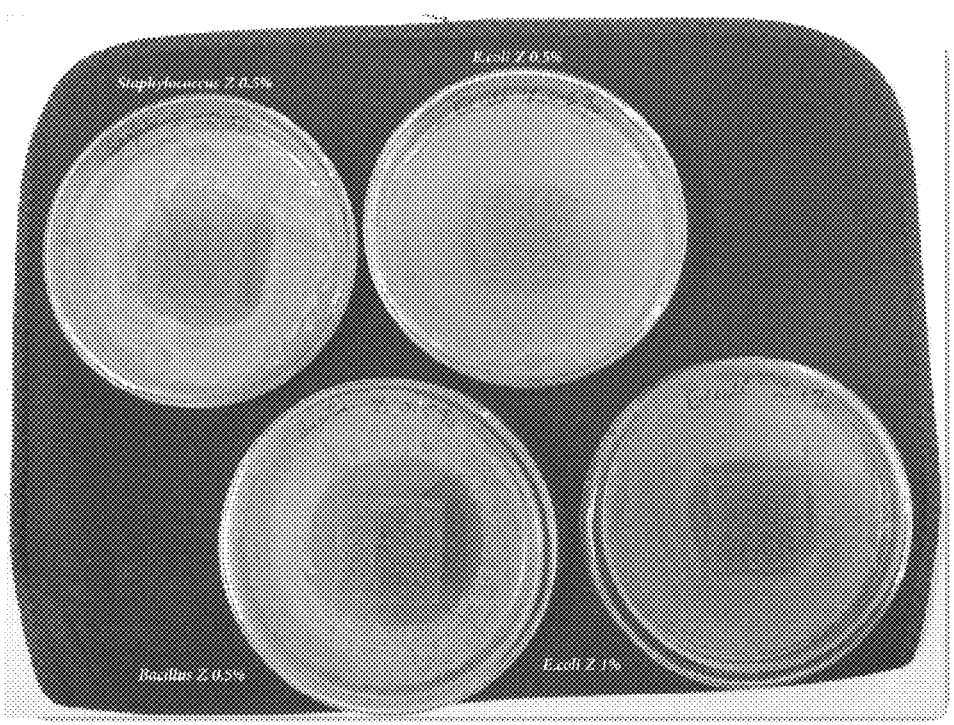
FIG. 8 includes an image of the results of zone of inhibition testing according to an embodiment including 0.5% zinc pyrithione ("ZPT") antimicrobial agent against *S. aureus, Bacillus*, and *E. coli*; and 1% ZPT against *E. coli*.
Figure 9:
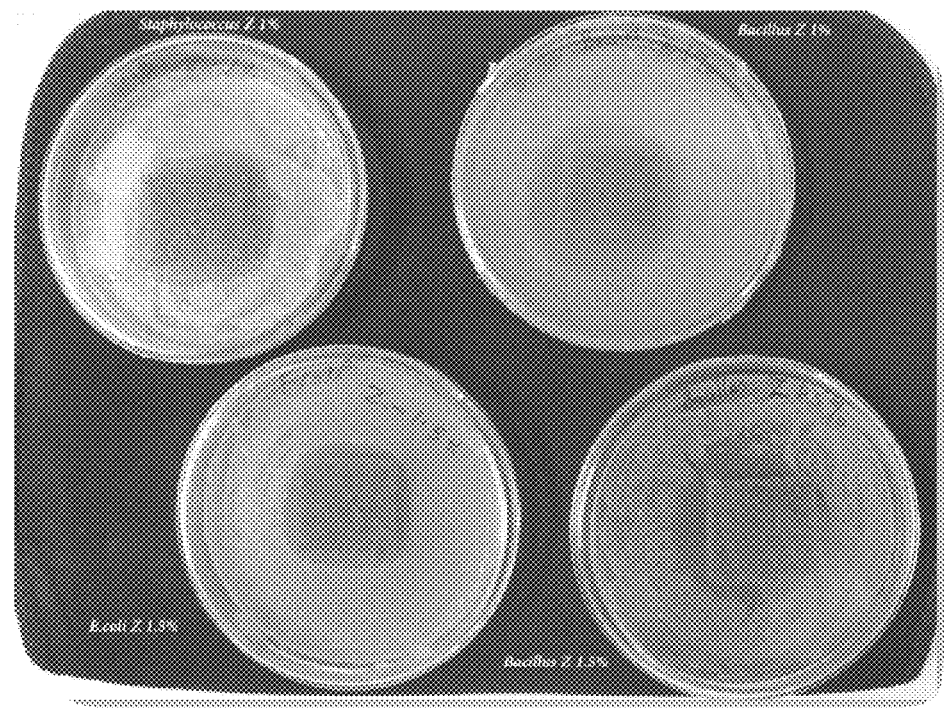
FIG. 9 includes an image of the results of zone of inhibition testing according to an embodiment including 1% ZPT antimicrobial agent against *S. aureus* and *Bacillus*; and 1.5% ZPT against *E. coli* and *Bacillus*.
Figure 10:
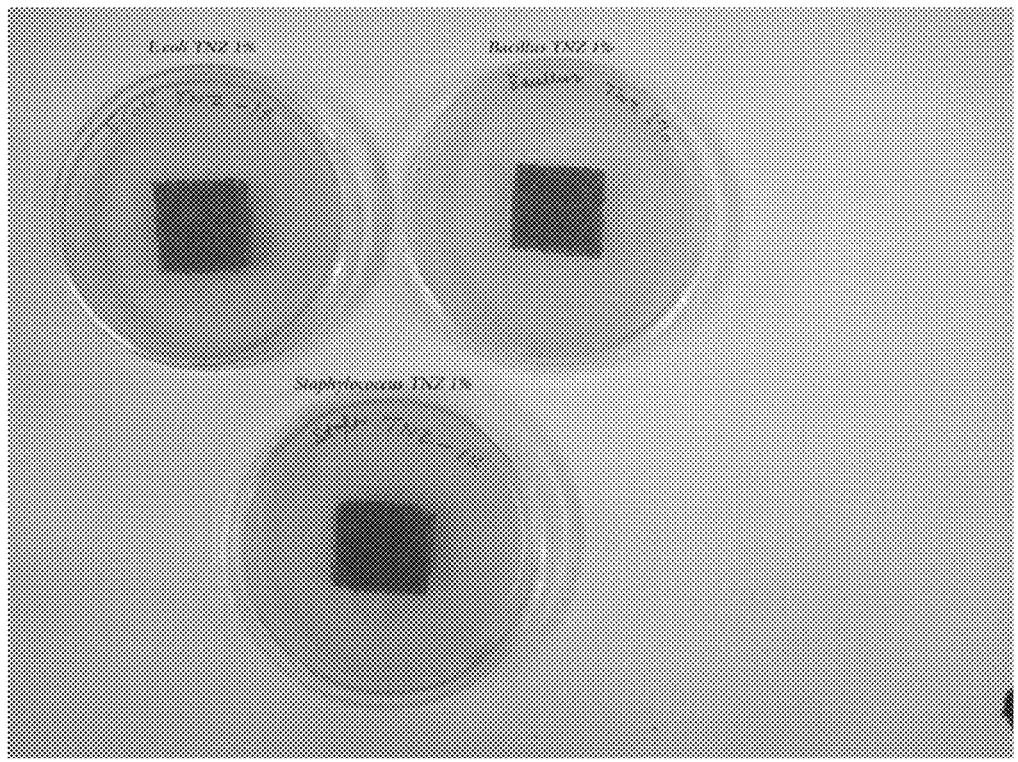
FIG. 10 includes an image of the results of zone of inhibition testing according to an embodiment including 1% of a 1:1 zinc pyrithione: triclosan mixture ("TNZ") antimicrobial agent against *E. coli, Bacillus*, and *S. aureus*.
Figure 11:
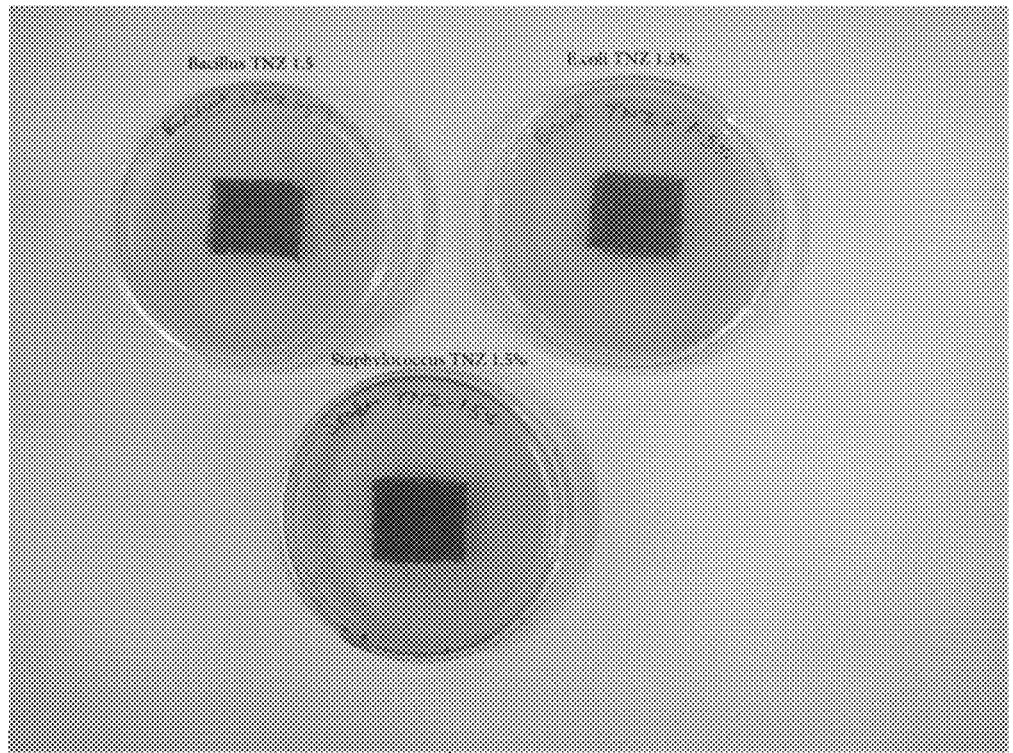
FIG. 11 includes an image of the results of zone of inhibition testing according to an embodiment including 1.5% of TNZ against *E. coli, Bacillus*, and *S. aureus*.

The inventive zinc pyrithione (ZPT) samples, comparative Triclosan (TN) samples, and comparative 1:1 zinc pyrithione: triclosan mixture (TNZ) samples were evaluated for broad spectrum antimicrobial activity with respect to organisms *S. aureus, K. pneumonia, E. coli*, and *Bacillus* according to the well known Kirby-Bauer antibiotic testing method. All samples were cut to the same size (approximately 1 in$^2$ (~2.54 cm$^2$)) and each sample was placed in separate petri dishes upon a substrate inoculated with a particular microbial organism. After 24 hours, the samples were observed to determine the average diameter of any existing zone of inhibition. The results are indicated below for inventive ZPT samples, comparative (TN) samples, and the comparative (TNZ) samples, in Tables H, I, and J, respectively. FIG. 7 shows zone of inhibition testing results for 1% TN against *K. pneumonia, E. coli, Bacillus*, and *S. aureus*. FIG. 8 shows zone of inhibition testing results for 0.5% ZPT against *S. aureus, Bacillus*, and *E. coli*; and 1% ZPT against *E. coli*. FIG. 9 shows zone of inhibition testing results for 1% ZPT against *S. aureus* and *Bacillus*; and 1.5% ZPT against *E. coli* and *Bacillus*. FIG. 10 shows zone of inhibition testing results for 1% TNZ against *E. coli, Bacillus*, and *S. aureus*. FIG. 11 shows zone of inhibition testing results for 1.5% TNZ against *E. coli, Bacillus*, and *S. aureus*.

TABLE H

ZPT Zone of Inhibition

| Active | Concentration | E. coli | S. aureus | Bacillus | K. pneumonia |
| --- | --- | --- | --- | --- | --- |
| | | Average Zone of Inhibition (diameter in cm) | | | |
| Zinc Pyrithione (ZPT) | 0.50 wt % | Reduced growth | 4.43 | 5.16 | Negative |
| | 1.0 wt % | 3.9 | 4.43 | 4.2 | 4.43 |
| | 1.5 wt % | 3.53 | 4.6 | 4.2 | 4.0 |

TABLE I

TN Zone of Inhibition

| Active | Concentration | E. coli | S. aureus | Bacillus | K. pneumonia |
| --- | --- | --- | --- | --- | --- |
| | | Average Zone of Inhibition (diameter in cm) | | | |
| Triclosan (TN) | 0.50 wt % | Negative | Negative | Negative | Negative |
| | 1.0 wt % | Negative | 7.5 | Negative | Negative |
| | 1.5 wt % | Negative | Reduced growth | 5.5 | Reduced growth |

TABLE J

TNZ Zone of Inhibition

| Active | Concentration | E. coli | S. aureus | Bacillus | K. pneumonia |
|---|---|---|---|---|---|
| | | Average Zone of Inhibition (diameter in cm) | | | |
| Triclosan and Zinc Pyrithione (TNZ) | 0.50 wt % | Negative | Negative | Negative | — |
| | 1.0 wt % | Negative | Negative | 3.6 | — |
| | 1.5 wt % | Reduced growth | 7.0 | Reduced growth | Reduced growth |

As illustrated in Tables H, I, and J, and shown in FIG. 7-11, the 1.5 wt % zinc pyrithione (ZPT) samples demonstrated excellent broad spectrum inhibition, while the (TN) samples and the (TNZ) samples did not. Table I, surprisingly illustrates that samples having triclosan (TN) as their only antimicrobial agent: at 0.5 wt % concentration had no antimicrobial activity; at 1.0 wt % concentration provided only positive inhibition of *S. aureus*; and at 1.5 wt % had measurable positive inhibition of Bacillus but only reduced growth of *S. aureus* and *K. pneumoniae*. The term "reduced growth" as used herein indicates that a clearly distinguishable circular zone of inhibition was not visible or that the distribution of the zone of inhibition was sporadic or uneven (from a top view of the area surrounding the sample in the petri dish) such that a uniform diameter zone of inhibition measurement could not be determined. More surprisingly, Table J illustrates that the antimicrobial mixture TNZ samples had the poorest results, mostly indicating negative inhibition at all concentrations.

G. Cyclic Abrasion Test

Additional samples were prepared as above. One sample was prepared having 1.5 wt % triclosan (TN). One sample was prepared having 1.0 wt % zinc pyrithione (ZPT) and one sample was prepared having 1.5 wt % ZPT. The samples were subjected to a cyclic abrasion test, which simulates the cleaning of an extensive number of kitchen utensils over an extended period of time, and the samples were then tested for antimicrobial inhibition according to the zone of inhibition test discussed above in order to determine whether the samples retained any antimicrobial properties. The cyclic abrasion test included scrubbing a 3 in$^2$ (corresponding to 7.62 cm$^2$) sample pads against an aluminum surface under a 2 kg load. All the data corresponds to the machine direction and the non-needled side of each sample. In cyclic abrasion testing for cut rates (CUT), the CUT was measured as the total amount of material removed from the aluminum surface during the test. In cyclic abrasion testing for grinding ratio, the grinding ratio (GR) was measured by the formula GR=CUT/SHED, where SHED=the amount of weight loss of the sample by the test process. The CUT, SHED, and GR data are obtained from a single test.

The results of the cyclic abrasion test are illustrated below in Table K.

TABLE K

Cyclic Abrasion Test

| Active agent | Cycles | E. coli | S. aureus | Bacillus | K. pneumonia |
|---|---|---|---|---|---|
| | | Average Zone of Inhibition (cm) | | | |
| TN - 1.5% | 1000 cycles | — | Reduced growth | — | 3.5 |
| | 2000 cycles | — | Reduced growth | — | 3.3 |
| | 3000 cycles | — | Reduced growth | — | 3.3 |
| | 5000 cycles | — | Reduced growth | — | 3.16 |
| ZPT - 1.0% | 5000 cycles | — | 4.55 | — | 3.6 |
| ZPT - 1.5% | 5000 cycles | — | 4.66 | — | 3.6 |

The results of the cyclic abrasion test indicate that the triclosan (TN) sample retained antimicrobial effectiveness after 5000 cycles only against *K. pneumoniae*. However, the inventive zinc pyrithione (ZPT) samples, at concentrations of 1.0% and 1.5%, still retained substantial antimicrobial effectiveness even after 5000 cycles against both *S. aureus* and *K. pneumonia*. The "—"(i.e., dash) indicates that no experiment was performed.

H. Accelerated Life Test

Two additional ZPT samples were prepared, one at a concentration of 1.0 wt %, and one at a concentration of 1.5 wt %. The ZPT samples were subjected to an accelerated life test to simulate real-time scrubbing and subsequently tested for antimicrobial inhibition according to the zone of inhibition test discussed above in order to determine the antimicrobial characteristics of the samples after a predetermined period of simulated use of the samples. The accelerated life test included placing a 1 in$^2$ (corresponding to 2.54 cm$^2$) sample into a container having a soap solution and subjecting the sample to a ball milling procedure for 3 hours.

The results of the accelerated life test are illustrated below in Table L.

TABLE L

Accelerated Life Test

| Active agent | Hours | E. coli | S. aureus | Bacillus | K. pneumonia |
|---|---|---|---|---|---|
| | | Average Zone of Inhibition (cm) | | | |
| ZPT - 1.0% | 3 hours | — | 5.2 | 4.8 | 4.3 |
| ZPT - 1.5% | 3 hours | — | 4.3 | 5.06 | 4.3 |

The results of the accelerated life test indicate that the inventive 1.0 wt % and 1.5 wt % ZPT samples still had substantial antimicrobial effectiveness against *S. aureus, Bacillus* and *K. pneumonia* even after the 3 hours of ball milling.

I. Antimicrobial Activity—ASTM: E2149-10-ZPT—Virgin Sample

Antimicrobial testing of an inventive ZPT abrasive article sample was conducted according to ASTM: E2149-10. In particular, the sample used was a virgin sample (i.e., a new sample not yet subjected to washing or other cleaning procedures). The results are provided below.

|  |  | No. of Bacteria per sample (CFU/ml) | | Percentage |
|---|---|---|---|---|
| Sample Identification | Test Organism | Inoculated Treated Sample at 0 hrs. (B) | Inoculated Treated Sample at 24 hrs. (A) | reduction of Bacteria (R) |
| ZPT (1.5 wt %) Virgin Sample | S. aureus | $1.85 \times 10^5$ | <10 | >99.99 |
| | E. coli | $2.10 \times 10^5$ | $5.8 \times 10^2$ | 99.72 |
| | K. pneumoniae | $1.75 \times 10^5$ | $4.6 \times 10^2$ | 99.73 |

(R) = 100 (B − A/B)

The test results indicate that the inventive samples had broad spectrum antimicrobial effectiveness against *S. aureus*, *E. coli*, and *K. pneumonia*.

J. Antimicrobial Activity—ASTM: E2149-10-ZPT Used Sample

Antimicrobial testing of an inventive ZPT abrasive article sample was conducted according to ASTM: E2149-10. In particular, the sample was a used sample (i.e., used to clean kitchen utensils). The sample was used to wash 300 kitchen utensils by hand over an extended period of time. Dynamic action was used during the washing and each of the utensils had food particles that needed to be scrubbed off. The results are provided below.

|  |  | No. of Bacteria per sample (CFU/ml) | | Percentage |
|---|---|---|---|---|
| Sample Identification | Test Organism | Inoculated Treated Sample at 0 hrs. (B) | Inoculated Treated Sample at 24 hrs. (A) | reduction of Bacteria (R) |
| ZPT (1.5 wt %) - Used Sample | S. aureus | $1.92 \times 10^5$ | <10 | >99.99 |
| | E. coli | $2.05 \times 10^5$ | $4.00 \times 10^4$ | 80.48 |
| | K. pneumoniae | $1.78 \times 10^5$ | $3.80 \times 10^4$ | 78.65 |

(R) = 100 (B − A/B)

The test results indicate that the inventive sample retained broad spectrum antimicrobial activity against *S. aureus*, *E. coli*, and *K. pneumonia* even after extended usage.

Note that not all of the activities described above in the general description or the examples are required, that a portion of a specific activity can not be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but can include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination.

Further, references to values stated in ranges include each and every value within that range. When the terms "about" or "approximately" precede a numerical value, such as when describing a numerical range, it is intended that the exact numerical value is also included. For example, a numerical range beginning at "about 25" is intended to also include a range that begins at exactly 25.

Embodiment 1. An abrasive article comprising:
a nonwoven substrate material impregnated with a first formulation;
wherein the first formulation has broad spectrum antimicrobial effectiveness against one or more microbial organisms; and
wherein the first formulation comprises a first antimicrobial agent and abrasive particles uniformly dispersed in a first polymer composition.

Embodiment 2. The abrasive article of Embodiment 1, further comprising;
a coating of a second formulation disposed on a first side and on a second side of the nonwoven substrate material,
wherein the second formulation has broad spectrum antimicrobial effectiveness against one or more microbial organisms; and
wherein the second formulation comprises a second antimicrobial agent and abrasive particles uniformly dispersed in a second polymer composition.

Embodiment 3. The abrasive article of Embodiment 2, wherein the broad spectrum antimicrobial effectiveness is defined as capable of killing at least about 75% of the population of an initial inoculation of one or more microbial organisms after 24 hours.

Embodiment 4. The abrasive article of Embodiment 1, wherein the one or more microbial organisms include *S. aureus*, and one or more of *K. pneumoniae*, *Bacillus*, and *E. coli*.

Embodiment 5. The abrasive article of Embodiment 2, wherein the one or more microbial organisms include *S. aureus*, and one or more of *K. pneumoniae*, *Bacillus*, and *E. coli*.

Embodiment 6. The abrasive article of Embodiment 5, wherein the broad spectrum antimicrobial effectiveness is defined as capable of killing at least about 75% of the population of an initial inoculation of *E. coli* after 24 hours, at least 75% of the population of an initial inoculation of *K. pneumonia* after 24 hours, and killing at least 95% of the population of an initial inoculation of *S. aureus* after 24 hours.

Embodiment 7. The abrasive article of Embodiment 2, wherein the abrasive article retains broad spectrum antimicrobial effectiveness over at least 5000 cycles of a Cycle Abrasion Test.

Embodiment 8. The abrasive article of Embodiment 1, wherein the first formulation comprises:
 0.1 wt % to 5.0 wt % of a first antimicrobial agent;
 20 wt % to 70 wt % of abrasive particles; and
 10 wt % to 60 wt % of a first polymer composition.

Embodiment 9. The abrasive article of Embodiment1, wherein the first antimicrobial agent comprises triclosan, triclocarban, polyhexamethylene biguanide, zinc pyrithione, salicylic acid, benzalkonium chloride, chloroxylenol, silver, or combinations thereof.

Embodiment 10. The abrasive article of Embodiment 9, wherein the silver comprises a silver solution, a silver suspension, a silver emulsion, a silver sol, a silver gel, solid silver, a silver powder, a silver composite material, or combinations thereof.

Embodiment 11. The abrasive article of Embodiment 3, wherein the first antimicrobial agent comprises zinc pyrithione.

Embodiment 12. The abrasive article of Embodiment 3, wherein the first antimicrobial agent consists essentially of zinc pyrithione.

Embodiment 13. The abrasive article of Embodiment 3, wherein the first antimicrobial agent consists of zinc pyrithione.

Embodiment 14. The abrasive article of Embodiment 1, wherein the first polymer composition comprises, phenolic resin, melamine formaldehyde resin, or combinations thereof.

Embodiment 15. The abrasive article of Embodiment 14, wherein the phenolic resin is a resole resin.

Embodiment 16. The abrasive article of Embodiment 1, further comprising a filler uniformly dispersed in the first polymer composition.

Embodiment 17. The abrasive article of Embodiment 16, wherein the first formulation comprises:
 0.1 wt % to 5.0 wt % first antimicrobial agent;
 20 wt % to 70 wt % abrasive particles;
 10 wt % to 60 wt % first polymer composition; and
 5 wt % to 30 wt % filler.

Embodiment 18. The abrasive article of Embodiment 2, wherein the second formulation comprises:
 0.1 wt % to 5.0 wt % second antimicrobial agent;
 20 wt % to 70 wt % abrasive particles; and
 10 wt % to 60 wt % second polymer composition.

Embodiment 19. The abrasive article of Embodiment 2, wherein the second antimicrobial agent comprises triclosan, triclocarban, polyhexamethylene biguanide, zinc pyrithione, salicylic acid, benzalkonium chloride, chloroxylenol, silver, or combinations thereof.

Embodiment 20. The abrasive article of Embodiment 19, wherein the silver comprises a silver solution, a silver suspension, a silver emulsion, a silver sol, a silver gel, solid silver, a silver powder, a silver composite material, or combinations thereof.

Embodiment 21. The abrasive article of Embodiment 19, wherein the antimicrobial agent comprises zinc pyrithione.

Embodiment 22. The abrasive article of Embodiment 19, wherein the second antimicrobial agent consists essentially of zinc pyrithione.

Embodiment 23. The abrasive article of Embodiment 19, wherein the second antimicrobial agent consists of zinc pyrithione.

Embodiment 24. The abrasive article of Embodiment 19, wherein the second polymer composition comprises a phenolic resin.

Embodiment 25. The abrasive article of Embodiment 24, wherein the phenolic resin is a resole resin.

Embodiment 26. The abrasive article of Embodiment 2, further comprising a filler uniformly dispersed in the second formulation.

Embodiment 27. The abrasive article of Embodiment 26, wherein the second formulation comprises:
 0.1 wt % to 5.0 wt % second antimicrobial agent;
 20 wt % to 70 wt % abrasive particles;
 10 wt % to 60 wt % second polymer composition; and
 5 wt % to 30 wt % filler.

Embodiment 28. The abrasive article of Embodiment 1, wherein the nonwoven substrate material comprises nylon, polyester, or a combination thereof.

Embodiment 29. The abrasive article of Embodiment 1, wherein the nonwoven substrate material has a weight per unit area of 100 GSM to 500 GSM prior to impregnation.

Embodiment 30. The abrasive article of Embodiment 1, wherein the nonwoven substrate material is impregnated with 500 GSM to 800 GSM of the first formulation.

Embodiment 31. The abrasive article of Embodiment 2, wherein the first side of the nonwoven substrate material is coated with 100 GSM to 300 GSM of the second formulation.

Embodiment 32. The abrasive article of Embodiment 2, wherein the second side of the nonwoven substrate material is coated with 100 GSM to 300 GSM of the second formulation.

Embodiment 33. A method of making an abrasive article comprising:
 preparing a first formulation;
 impregnating a nonwoven substrate material with the first formulation,
 preparing a second formulation;
 disposing the second formulation on a first side of the nonwoven material substrate; and
 disposing the second formulation on a second side of the nonwoven material substrate to form the abrasive article,
 wherein the abrasive article has broad spectrum antimicrobial effectiveness against one or more microbial organisms.

Embodiment 34. The method of Embodiment 33, wherein the one or more microbial organisms includes *S. aureus*, and one or more of *K. pneumoniae, Bacillus*, and *E. coli*.

Embodiment 35. The method of Embodiment 33, wherein preparing the first formulation comprises:
  mixing together a first antimicrobial agent, a first polymer composition, and abrasive particles, wherein the first antimicrobial agent and abrasive particles are uniformly dispersed in the first polymer composition.

Embodiment 36. The method of Embodiment 33, wherein preparing the second formulation comprises:
  mixing together a second antimicrobial agent, a second polymer composition, and abrasive particles, wherein the second antimicrobial agent and abrasive particles are uniformly dispersed in the second polymer composition.

Embodiment 37. The method of Embodiment 33, wherein preparing the first formulation comprises mixing together ingredients comprising:
  0.1 wt % to 5 wt % first antimicrobial agent;
  10 wt % to 60 wt % phenol formaldehyde resin;
  2 wt % to 20 wt % melamine formaldehyde resin;
  5 wt % to 30 wt % filler;
  20 wt % to 70 wt % abrasive particles; and
  2 wt % to 25 wt % water.

Embodiment 38. The method of Embodiment 33, wherein preparing the second formulation comprises mixing together ingredients comprising
  0.1 wt % to 5 wt % second antimicrobial agent;
  10 wt % to 25 wt % water
  10 wt % to 60 wt % phenol formaldehyde resin
  5 wt % to 30 wt % filler; and
  20 wt % to 70 wt % abrasive particles.

Embodiment 39. The method of Embodiment 33, wherein the nonwoven substrate material is impregnated with 200 GSM to 2000 GSM of the first formulation.

Embodiment 40. The method of Embodiment 33, wherein the first side of the nonwoven substrate material is coated with 100 GSM to 1000 GSM of the second formulation.

Embodiment 41. The method of Embodiment 33, wherein the second side of the nonwoven substrate material is coated with 100 GSM to 1000 GSM of the second formulation.

What is claimed is:

1. An abrasive article comprising:
  a nonwoven substrate material impregnated with a first formulation;
  wherein the first formulation has broad spectrum antimicrobial effectiveness against one or more microbial organisms; and
  wherein the first formulation comprises a first antimicrobial agent and abrasive particles uniformly dispersed in a first polymer composition; and
  a coating of a second formulation disposed on a first side and on a second side of the nonwoven substrate material,
  wherein the second formulation has broad spectrum antimicrobial effectiveness against one or more microbial organisms; and
  wherein the second formulation comprises a second antimicrobial agent and abrasive particles uniformly dispersed in a second polymer composition.

2. The abrasive article of claim 1, wherein the broad spectrum antimicrobial effectiveness is defined as capable of killing at least 75% of the population of an initial inoculation of one or more microbial organisms after 24 hours.

3. The abrasive article of claim 1, wherein the one or more microbial organisms include *S. aureus*, and one or more of *K. pneumoniae, Bacillus*, and *E. coli*.

4. The abrasive article of claim 1, wherein the one or more microbial organisms include *S. aureus*, and one or more of *K. pneumoniae, Bacillus*, and *E. coli*.

5. The abrasive article of claim 4, wherein the broad spectrum antimicrobial effectiveness is defined as capable of killing at least about 75% of the population of an initial inoculation of *E. coli* after 24 hours, at least 75% of the population of an initial inoculation of *K. pneumonia* after 24 hours, and killing at least 95% of the population of an initial inoculation of *S. aureus* after 24 hours.

6. The abrasive article of claim 1, wherein the abrasive article retains broad spectrum antimicrobial effectiveness over at least 5000 cycles of a Cycle Abrasion Test.

7. The abrasive article of claim 1, wherein the first formulation comprises:
  0.1 wt % to 5.0 wt % of a first antimicrobial agent;
  20 wt % to 70 wt % of abrasive particles; and
  10 wt % to 60 wt % of a first polymer composition.

8. The abrasive article of claim 1, wherein the first antimicrobial agent comprises triclosan, triclocarban, polyhexamethylene biguanide, zinc pyrithione, salicylic acid, benzalkonium chloride, chloroxylenol, silver, or combinations thereof.

9. The abrasive article of claim 2, wherein the first antimicrobial agent comprises zinc pyrithione.

10. The abrasive article of claim 1, further comprising a filler uniformly dispersed in the first polymer composition.

11. The abrasive article of claim 10, wherein the first formulation comprises:
  0.1 wt % to 5.0 wt % first antimicrobial agent;
  20 wt % to 70 wt % abrasive particles;
  10 wt % to 60 wt % first polymer composition; and
  5 wt % to 30 wt % filler.

12. The abrasive article of claim 1, wherein the second formulation comprises:
  0.1 wt % to 5.0 wt % second antimicrobial agent;
  20 wt % to 70 wt % abrasive particles; and
  10 wt % to 60 wt % second polymer composition.

13. The abrasive article of claim 1, wherein the second antimicrobial agent comprises triclosan, triclocarban, polyhexamethylene biguanide, zinc pyrithione, salicylic acid, benzalkonium chloride, chloroxylenol, silver, or combinations thereof.

14. The abrasive article of claim 13, wherein the second antimicrobial agent comprises zinc pyrithione.

15. The abrasive article of claim 1, further comprising a filler uniformly dispersed in the second formulation.

16. The abrasive article of claim 15, wherein the second formulation comprises:
  0.1 wt % to 5.0 wt % second antimicrobial agent;
  20 wt % to 70 wt % abrasive particles;
  10 wt % to 60 wt % second polymer composition; and
  5 wt % to 30 wt % filler.

17. A method of making an abrasive article comprising:
  preparing a first formulation;
  impregnating a nonwoven substrate material with the first formulation,
  preparing a second formulation;
  disposing the second formulation on a first side of the nonwoven material substrate; and
  disposing the second formulation on a second side of the nonwoven material substrate to form the abrasive article,
  wherein the abrasive article has broad spectrum antimicrobial effectiveness against one or more microbial organisms.

18. The method of claim 17, wherein preparing the first formulation comprises:
mixing together a first antimicrobial agent, a first polymer composition, and abrasive particles, wherein the first antimicrobial agent and abrasive particles are uniformly dispersed in the first polymer composition.

19. The method of claim 17, wherein preparing the first formulation comprises mixing together ingredients comprising:
0.1 wt % to 5 wt % first antimicrobial agent;
10 wt % to 60 wt % phenol formaldehyde resin;
2 wt % to 20 wt % melamine formaldehyde resin;
5 wt % to 30 wt % filler;
20 wt % to 70 wt % abrasive particles; and
2 wt % to 25 wt % water.

20. An abrasive article comprising:
a nonwoven substrate material impregnated with a first formulation;
wherein the first formulation has broad spectrum antimicrobial effectiveness against one or more microbial organisms;
wherein the first formulation comprises a first antimicrobial agent and abrasive particles uniformly dispersed in a first polymer composition;
wherein the broad spectrum antimicrobial effectiveness is defined as capable of killing at least 75% of the population of an initial inoculation of one or more microbial organisms after 24 hours; and
wherein the one or more microbial organisms include *S. aureus*, and one or more of *K. pneumoniae, Bacillus*, and *E. coli*.

* * * * *